United States Patent [19]

Murphy

[11] Patent Number: 5,107,899

[45] Date of Patent: Apr. 28, 1992

[54] PNEUMATIC CONTROL SYSTEM

[76] Inventor: Gregory Murphy, 12351 NW. 29th St., P.O. Box 15966, Sunrise, Fla. 33318

[21] Appl. No.: 616,782

[22] Filed: Nov. 20, 1990

Related U.S. Application Data

[63] Continuation of Ser. No. 384,249, Jul. 24, 1989, abandoned, which is a continuation of Ser. No. 158,321, Feb. 19, 1988, abandoned.

[51] Int. Cl.$^5$ ............................................. F16K 27/00
[52] U.S. Cl. ...................................... 137/884; 433/28
[58] Field of Search ................... 433/28; 137/884, 269

[56] References Cited

U.S. PATENT DOCUMENTS

| | | | |
|---|---|---|---|
| 3,638,310 | 2/1972 | Austin, Jr. | 433/28 |
| 4,188,976 | 2/1980 | Austin, Jr. | 433/28 X |
| 4,332,555 | 6/1982 | Richardson | 433/28 |
| 4,676,750 | 6/1987 | Mason | 433/28 X |
| 4,806,099 | 2/1989 | Peralta | 433/28 |

FOREIGN PATENT DOCUMENTS 2083752  3/1982  United Kingdom ................. 433/28

Primary Examiner—John C. Fox
Attorney, Agent, or Firm—Malin, Haley, McHale, DiMaggio & Crosby

[57] ABSTRACT

This is a dental air and water supply apparatus for selectively and automatically controlling the supply of drive air and/or air and water coolants to any one dental drill or dental handpiece in a dental tool system. The dental apparatus includes a plurality of separately replaceable modular pneumatic circuit blocks and connecting manifolds that are fed by a master block and distribution manifold. The modular pneumatic circuit blocks are modular and separate from the distribution manifold and thereby provides easy repair of the apparatus.

16 Claims, 20 Drawing Sheets

PNEUMATIC CONTROL SYSTEM

This application is a continuation of Ser. No. 7/384,249, filed Jul. 24, 1989, now abandoned which in turn was a continuation of Ser. No. 07/158,321 filed on Feb. 19, 1988 now abandoned.

BACKGROUND OF THE INVENTION

Most dental handpieces today provide a variety of functions including an air driven drill, air cooling for the drill, water for rinsing the mouth, and air to move debris from the mouth and to purge water from the water outlet. To be able to provide individual control of these functions including using a foot control, a switching control system is required. Many types of switching control systems have been devised in the past. Some switching control systems require switches to be manually turned on and off to activate a particular function on the handpiece. Some systems use air activated diaphragms to control certain functions. Still others require a combination of electrical circuitry with pneumatic lines to activate the respective functions. In present use, most control switching units are filled with a maze of wires and tubing connectors or both that make the switching control systems complex, difficult and expensive to manufacture, and difficult to repair or replace.

SUMMARY OF THE INVENTION

The present invention provides a modular simple control system, easy to manufacture, repair or replace. The system is a pneumatic air and water control apparatus for selectively and automatically controlling the supply of drive air, air and water to any one of a plurality of dental handpieces in a dental tool system. The system includes a plurality of separately replaceable modular pneumatic circuit blocks and connecting manifolds that are fed by a master module and distribution manifold. The pneumatic circuit blocks are modular and separate from the distribution manifold and thereby provide easy repair or replacement of the modules. In addition, the modules may be readily linked thereby easily expanding the system.

The system includes a master module, having switches such as a master on/off switch and on/off indicator, which module controls the entire unit. Also included is a chip air flow adjustment valve, a wet/dry switch for water signaling and a handpiece pressure gauge for indicating the back pressure on the air turbine of the drill. It is to be noted that the aforementioned switches, valves and gauges are pneumatic and therefore non-electrical switches.

The master module is mounted upon a distribution manifold through which all air and water feeding lines are connected, such as handpiece drive air, chip air, regulated and unregulated air, unregulated air return and water. Also located in the manifold are two flow adjustment screws for the air and water to the syringe.

Attached to the side of the distribution manifold is one or more control manifolds, depending upon the needs of the dentist. The control manifold houses the flow adjustment screw for air coolant flow control and drive air flow pressure control to the handpiece. Also a purge valve is connected to the control manifold for each individual module which purges water from the tip of the handpiece with air. In addition, the control manifold feeds input and receives output of air and water from the pneumatic circuit module.

The individual pneumatic circuit module are mounted on the upper surface of the control manifold. Contained in the pneumatic circuit module are the main air drive and water valves and the air and water coolant flow adjustment valves. In conjunction with each pneumatic circuit module, there is an external handpiece holder and switch which signals the pneumatic circuit module whether or not the handpiece is residing in the holder via an air signal.

OBJECTS OF THE INVENTION

It is an object of this invention to control all the functions in a dental handpiece.

Another object of this invention is to allow trained or untrained personnel to repair this system and to be able to perform all repairs with little or no effort compared to the effort presently required to repair existing systems.

Another object of this invention is to use pneumatic switches containing pneumatic AND-gates, as drive air and water valves, thereby making the entire control 100% pneumatically operated.

A further object of this invention is to provide a purge function wherein air pressure is used to purge water out of the water line in a handpiece after use on a patient.

A still further object of the invention is to provide a dental air and water supply apparatus wherein additional units corresponding to additional handpieces may easily be added depending upon the dentist's needs.

Yet another object of the invention is to provide a plurality of control manifolds and modules wherein each control manifold and module is used to control a different dental handpiece.

A further object of the invention is to provide a plurality of control modules wherein each control module includes an air exhaust port for the exhaust air from the drill turbine, each port including a diffuser to reduce the amount of noise generated by the exhausting air.

It is a further object of the invention to achieve the foregoing objects and more by using modular design and construction.

In accordance with these and other objects which will be apparent hereinafter, the instant invention will now be described with particular reference to the accompanying drawings.

DETAILED DESCRIPTION OF ONE EMBODIMENT OF THE INVENTION

Figure 1A:
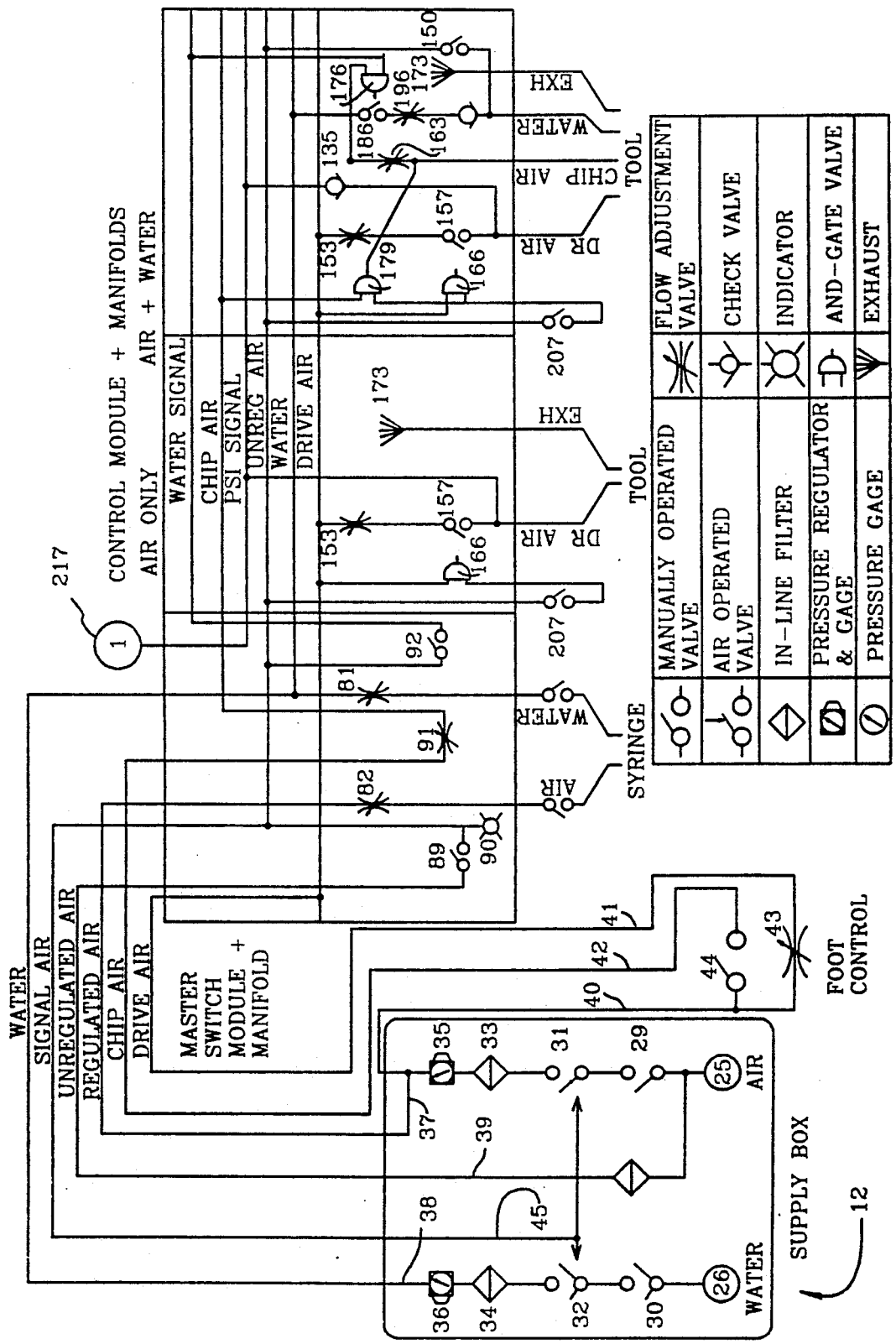
FIG. 1A is a schematic of the pneumatic tool control system.

Referring first to FIG. 1A, a schematic diagram of the control system is shown. One part of the system is the supply box 12 shown in detail in FIG. 2. As can be seen from FIG. 2, supply box 12 provides a source of air from a compressor 25 and a source of water from a water supply 26.

Figure 2:
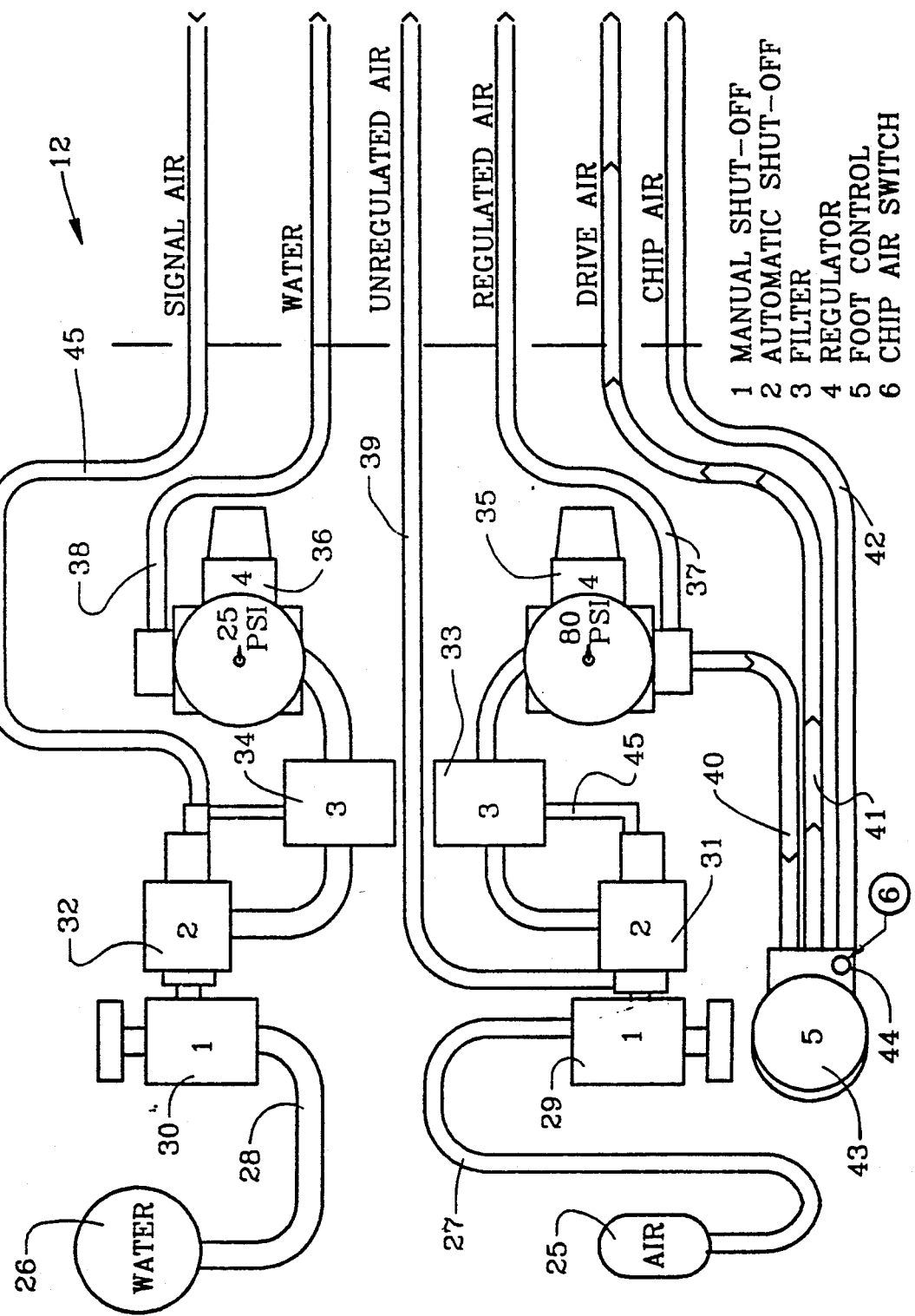
FIG. 2 is a schematic of the air and water paths in the system illustrating the support equipment supplying air and water to the air and water consuming apparatus.

Looking at the air supply function of supply box 12 in detail as shown in FIGS. 1A and 2, it is seen that air from compressor 25 is supplied to manual air shut off valve 29 through air supply line 27. Manual air shut off valve 29 allows the entire system to be shut off from the air from compressor 25. Compressor 25 may include an air storage tank in addition to a compressor. The automatic air shut off valve 31 is connected to manual air shut off valve 29.

Connected to the junction of manual air shut off valve 29 and automatic air shut off valve 31 is unregulated air line 39 which provides a source of air pressure whenever manual air shut off valve 29 is opened regardless of the condition of automatic air shut off valve 31. The function of unregulated air line 39 will be described in more detail later. Automatic air shut off valve 31 is connected to air regulator 35 through a line having an air filter 33 for filtering the air from air compressor 25. Air regulator 35 provides a variable pressure source to the system. The pressure from air regulator 35 varies from 0 to 80 pounds per square inch and is manually adjustable by the user of the system.

Automatic air shut off valve 31 is controlled by signal air return line 45 so that the operative or inoperative condition of automatic air shut off valve 31 depends on whether signal air return line 45 is pressurized or not as will be described hereafter.

Figure 1B:
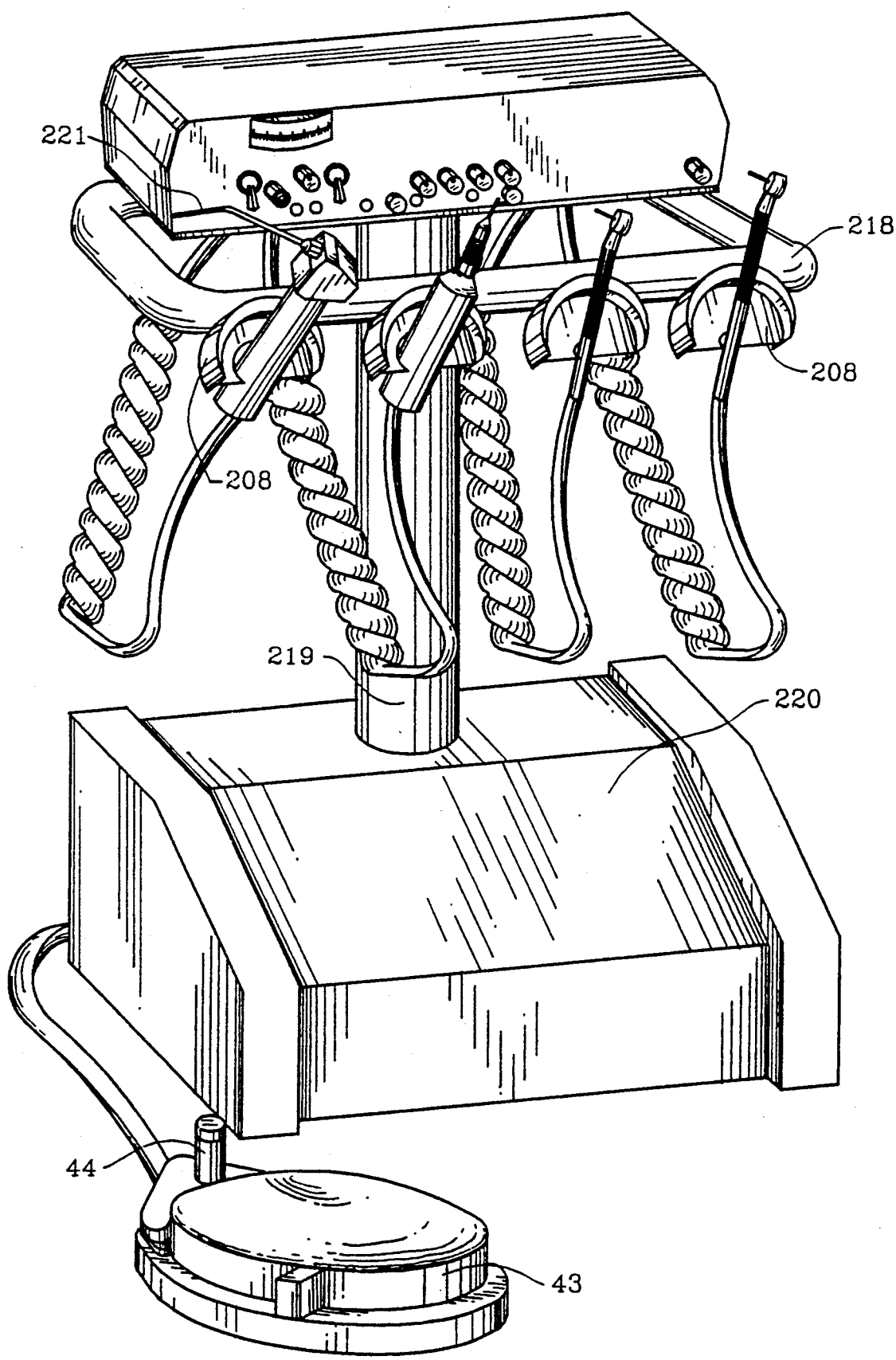
FIG. 1B is a front view of the pneumatic dental air and/or water supply apparatus.

Air leaving air regulator 35 is designated drive air and leaves supply box 12 through air supply line 40 which is connected to drive air foot control 43 (FIGS. 1A and 1B). Drive air foot control 43 allows the user to pass drive air to the system by the depression of drive air foot control 43. When drive air foot control 43 is depressed, air passes through it into drive air line 41 into the manifold 88 at ultimately to power the air turbine of a dental handpiece 315 (FIG. 10) as will be explained hereafter.

The water supply function of supply box 12 will now be described in detail with reference to FIGS. 1A and 2.

Water from water supply 26 is supplied to manual shut off valve 30 through water supply line 28. Manual water shut off valve 30 allows the user to manually control whether water may be passed further into the system. Manual water shut off valve 30 is attached to automatic water shut off valve 32. By analogy to automatic air shut off valve 31, automatic water shut off valve 32 is controlled by the presence or absence of signal air pressure from signal air return line 45 which is connected to automatic water shut off valve 32. If automatic water shut off valve 32 is activated by air pressure within signal air return line 45, water from water supply 26 then passes through manual water shut off valve 30, automatic water shut off valve 32 through water filter 34 into water pressure regulator 36.

Water pressure regulator 36 controls the pressure available to the system within a range of 0 to 25 pounds per square inch as determined by the user. After passing through water regulator 36, water leaves supply unit 12 through water line 38. It is to be noted that signal air return line 45 which controls both automatic air shut off valve 31 and automatic water shut off valve 32, extends out of supply box 12 on one end and connects both automatic air and water shut off valves 31, 32.

Referring again to drive air foot control 43, air from air supply line 40, in addition to passing through drive air foot control 43 to exit through a drive air line 41, may also pass to chip air line 42 through the actuation of chip air button 44 located on drive air foot control 43 (FIGS. 1B and 2). Depressing chip air button 44 allows air from air supply line 40 to enter chip air line 42 for a purpose which will be described hereafter.

Figure 3A:
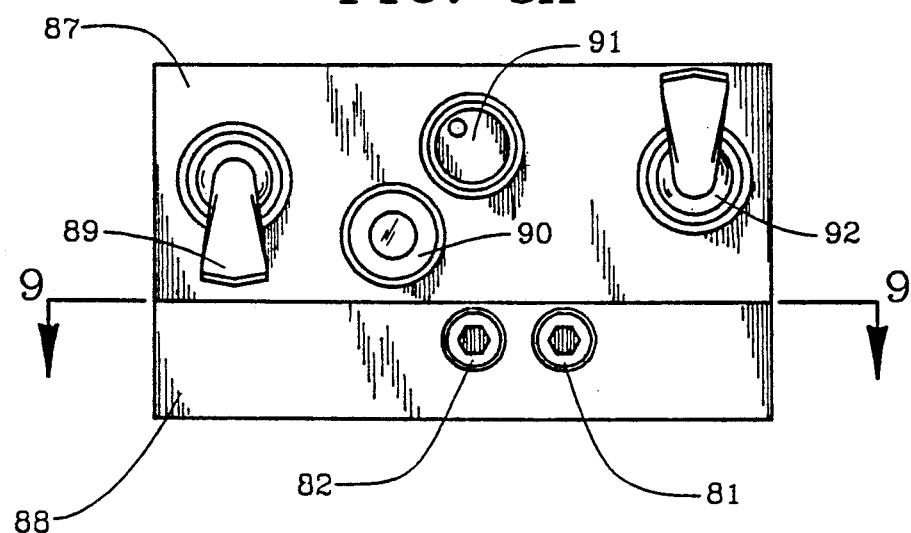
FIG. 3A is a front view of master switch module and its manifold.
Figure 3B:
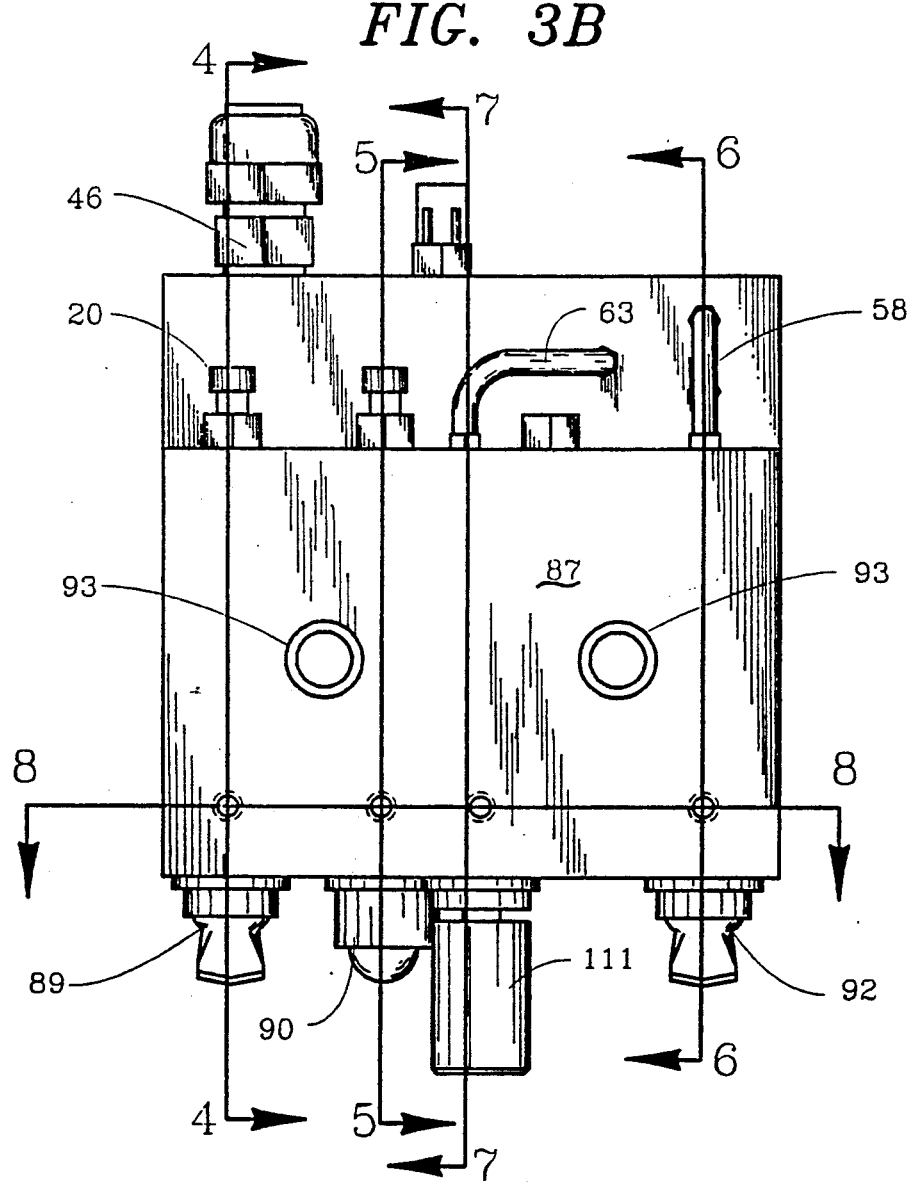
FIG. 3B shows the plan view of the master switch module in FIG. 3A.
Figure 4:
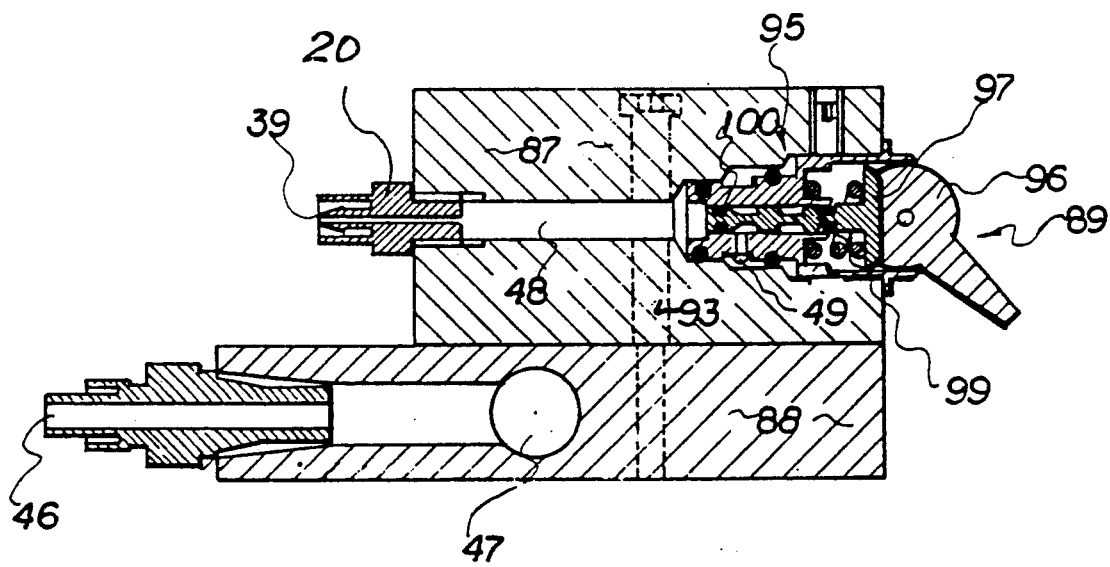
FIG. 4 is a cross-section taken along lines 4—4 in FIG. 3B showing a left side vertical cross-section view of the master on/off switch module and manifold illustrating the drive air and unregulated air passages.

As mentioned above, unregulated air leaves supply box 12 through unregulated air line 39. This unregulated air has the same air pressure that compressor 25 supplies. The unregulated air enters master switch module 87 (shown schematically in FIG. 1A) through connector 20 (FIG. 4). Connector 20 connects unregulated air line 39 to unregulated air inlet passage 48 which in turn is connected to on/off switch 89 (FIGS. 3A, 3B and 4) which is a common pneumatic toggle switch. When on/off switch 89 is in the "off" position air within unregulated air inlet passage 48 is prevented from entering unregulated air connecting passage 49 for distribution into the system by O-rings 100 along a plunger located within a chamber above unregulated air connecting passage 49. When on/off switch 89 is moved to the "on" position, the O-rings are displaced allowing air within unregulated air inlet passage 48 to move past the O-rings into unregulated air connecting passage 49.

Figure 3C:
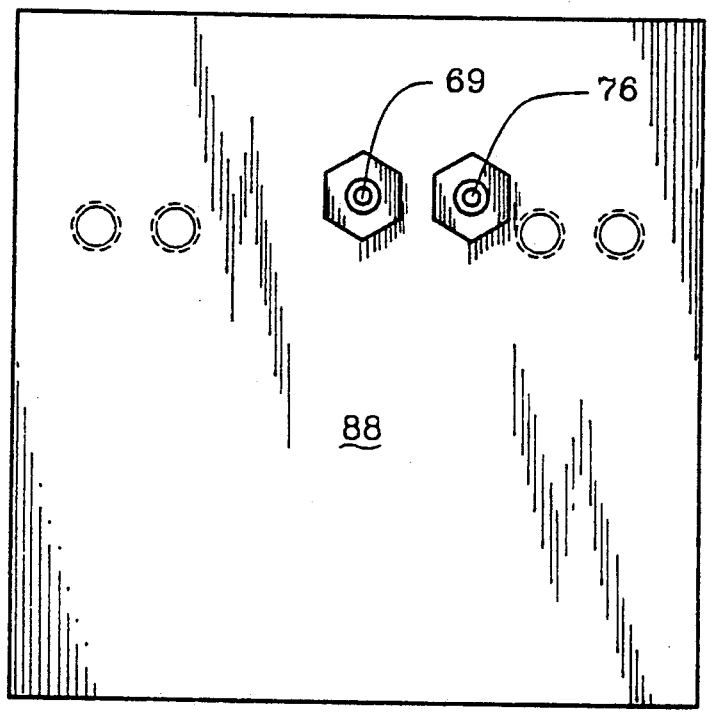
FIG. 3C shows the bottom of the manifold in FIG. 3A.
Figure 3D:
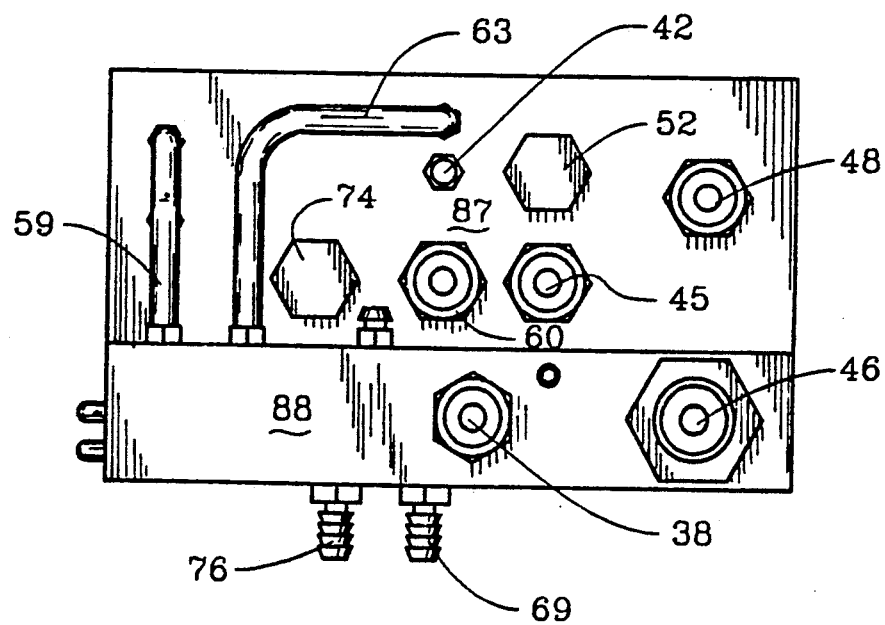
FIG. 3D shows the rear of the manifold and master switch module in FIG. 3A.
Figure 5:
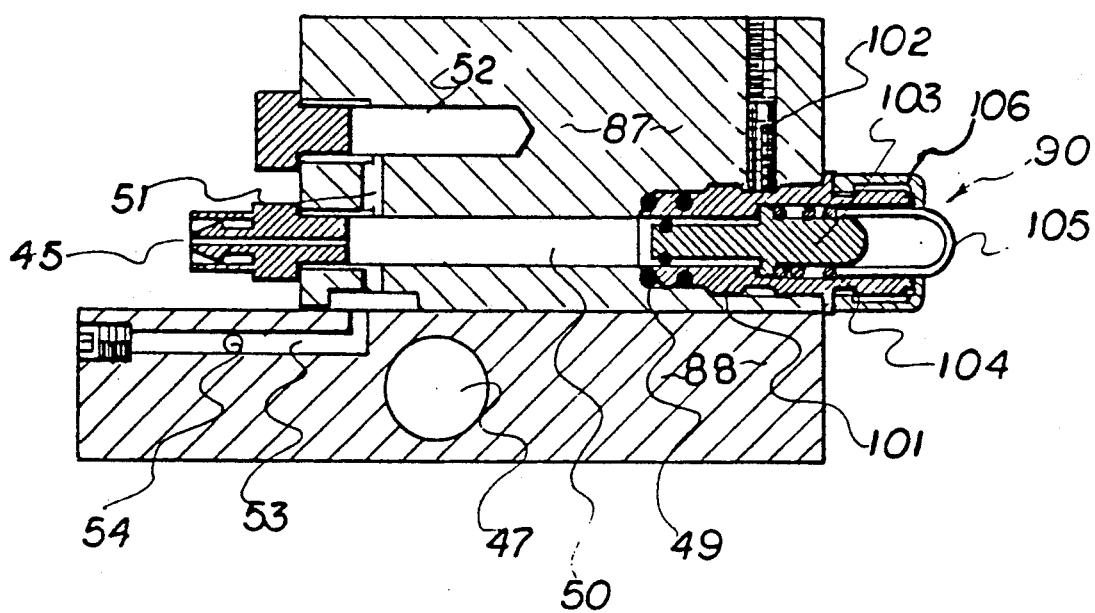
FIG. 5 is a cross-section taken along lines 5—5 in FIG. 3B showing a left side vertical cross-section view of pneumatic indicator and unregulated air passages.

Unregulated air connecting passage 49 is connected to chamber 50 (FIG. 5) which distributes the unregulated air in three ways. First, the unregulated air passes out of master module 87 and into master manifold 88 through passage 53 (FIG. 5). As shown in FIGS. 3A, 3B and 3D, master module 87 is attached to the top of master manifold 88 by module retainment screws 93 which extend through master module 87 into master manifold 88. Connected to passage 53 in master manifold 88 is unregulated air distribution passage 54 which runs through master manifold 88 so that unregulated air may be passed from master manifold 88 to the abutting control manifold 115 through passage 54.

The other place unregulated air is directed from chamber 50 is back to supply box 12 through signal air return line 45 (FIG. 5). As previously mentioned, signal air return line 45 is connected to both automatic air and water shut off valves 31, 32. With this connection, when unregulated air is presented to the master module 87 through unregulated air line 39 and on/off switch 89 is placed in the "on" position, unregulated air is returned to automatic air and water shut off valves 31, 32 in supply box 12 to activate valves 31, 32 so that drive air, chip air and air coolant as well as water is made available to the system.

Connected to chamber 50 is a pneumatic indicator 90 (FIGS. 3A and 5), such as is common in the industry, which, through the presence of unregulated air in chamber 50 from master on/off switch 89, when in the "on" position, indicates that master switch 89 is turned on and the drive air, chip air and coolant, and water are available for the system.

Figure 3E:
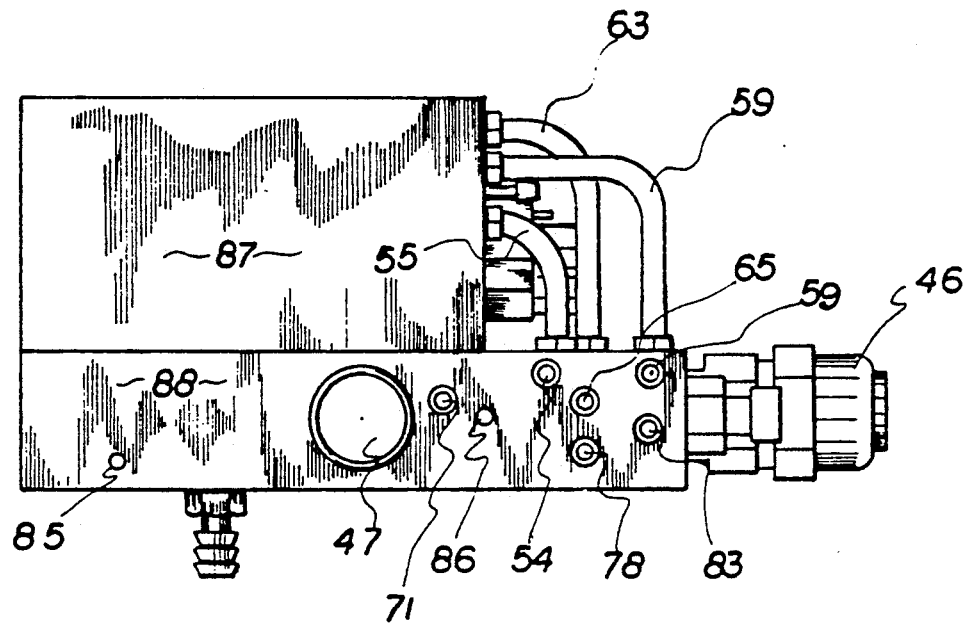
FIG. 3E shows the right side of the master switch and manifold in FIG. 3B.

Once master on/off switch 89 has been activated and unregulated air made available to the downstream unregulated air line 39, the unregulated air is available for the purposes of purging water out of the tip of a air/water syringe 221 (FIGS. 1B and 1D) and, providing a source of air pressure for the handpiece holder switches 208 (FIGS. 1B, 1D and 20–22) which control unregulated air for signaling purposes as shall be described hereafter. As stated, unregulated air leaves master switch module 87 through passage 53 in master switch manifold 88. There, the unregulated air is distributed via unregulated air distribution passage 54 (FIGS. 3E and 5).

Manifold 88 is essentially a block which abuts master switch module 87 on its top side and a control module 115 on one side (FIG. 1E) as will be described hereafter. Manifold 88 has a series of passages and openings which allow air and water to pass through it. The openings in manifold 88 may be connected to master module 87, control manifold 115, or to the exterior of manifold 88. In this way, air and water may enter or leave manifold 88 from master module 87, control manifold 115, or from tubing or devices connected to the exterior of master manifold 87.

Figure 10A:
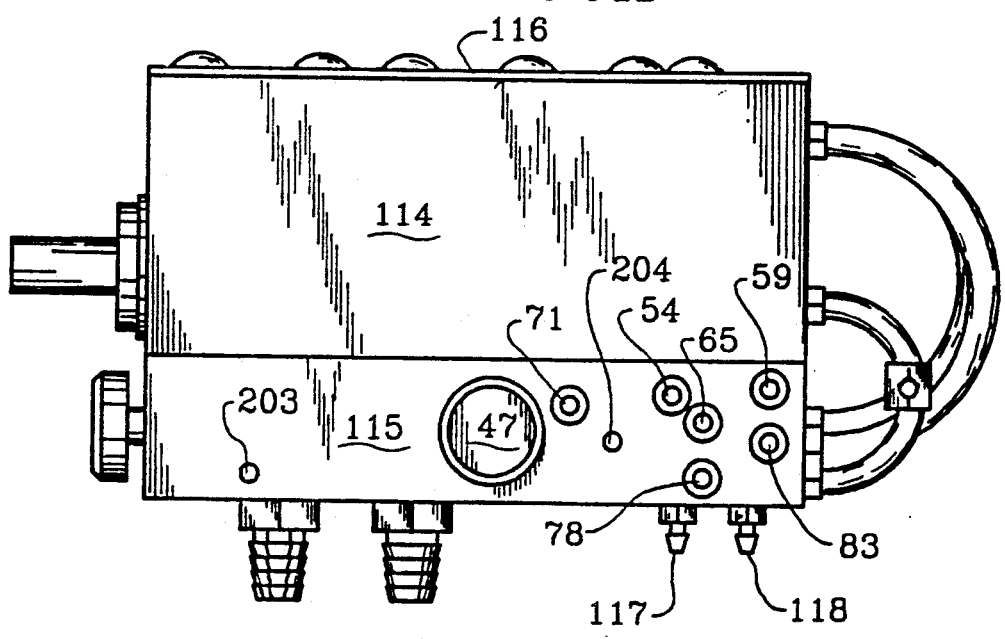
FIG. 10A is a side view of an air and water control module and manifold taken along lines 10A—10A in FIG. 1E.
Figure 10B:
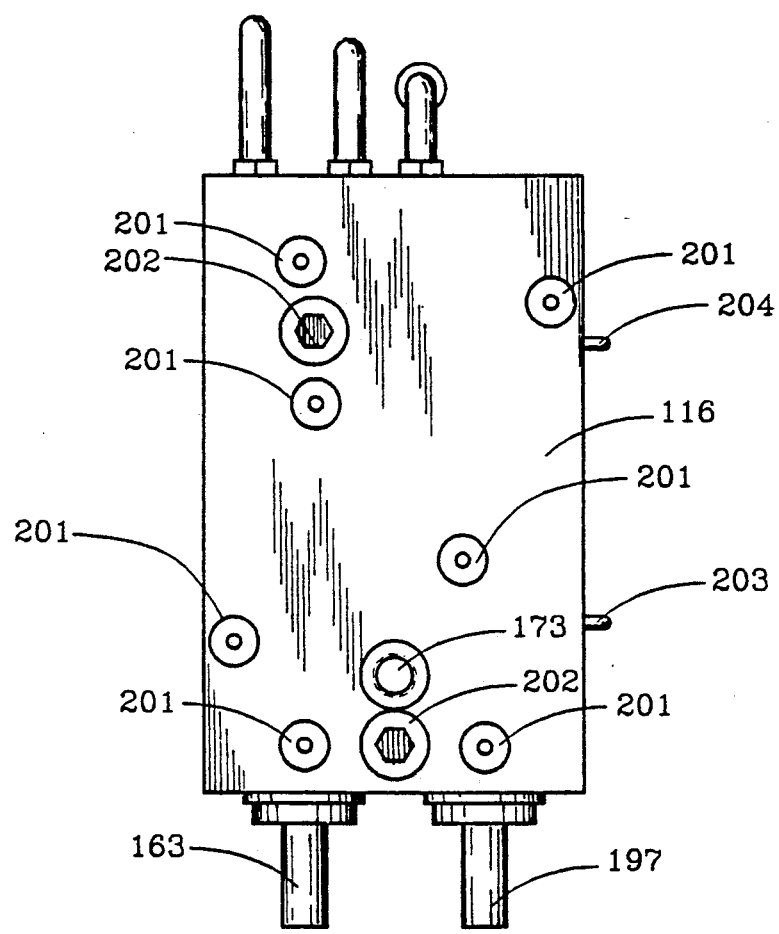
FIG. 10B is a plan view of an air and water manifold.
Figure 10C:
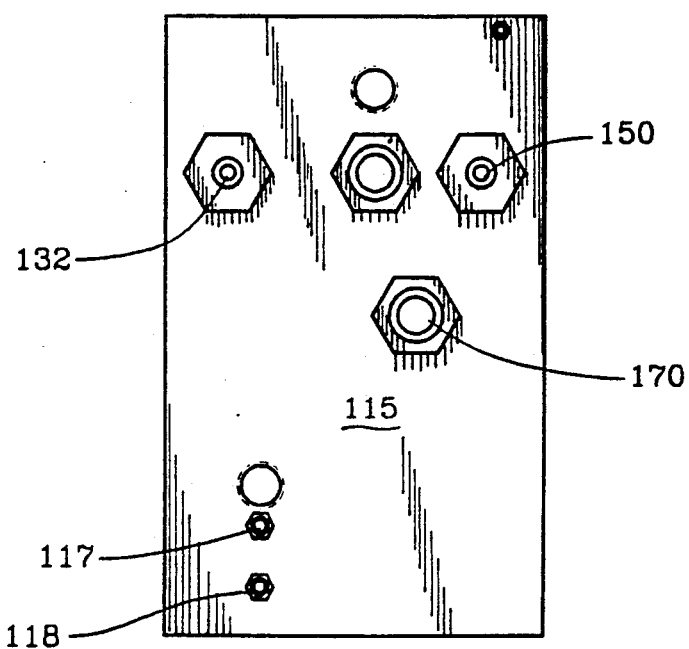
FIG. 10C is a bottom view of an air and water manifold.
Figure 10D:
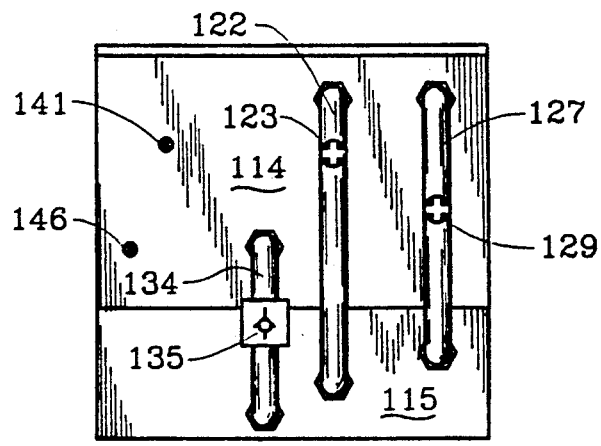
FIG. 10D is a rear view of the control module and manifold illustrated in FIGS. 10A, 10B and 10C.
Figure 11:
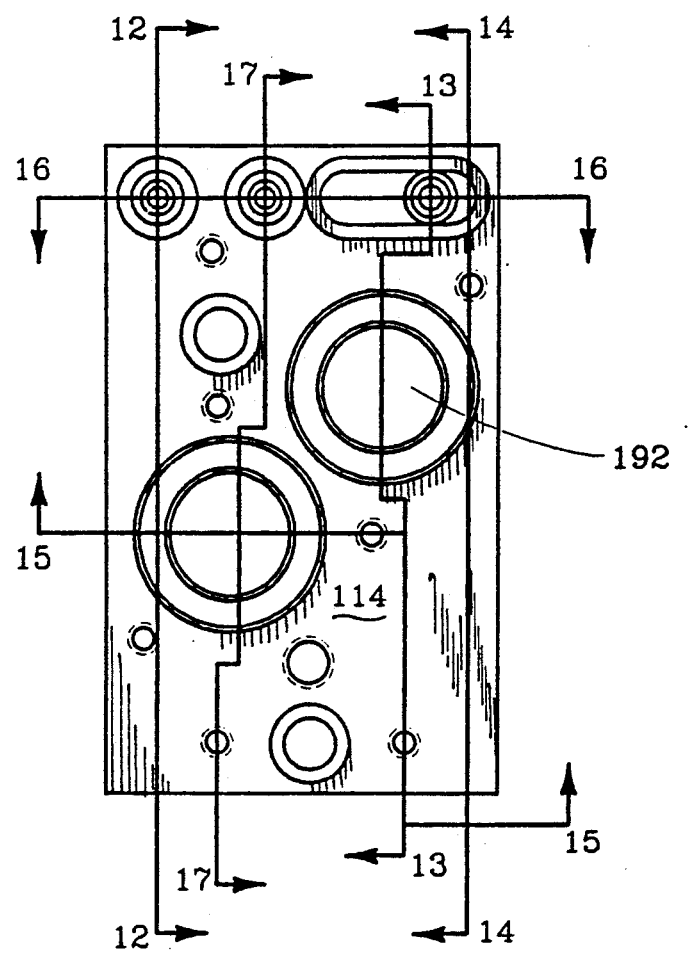
FIG. 11 is a plan view of the control module shown in FIG. 10B with its cover plate removed.

Air in drive air line 41, which has just come from the drive air foot control 43 enters master module 88 through drive air inlet passage 46 (FIGS. 3D and 4). Drive air inlet passage 46 is connected to drive air distribution passage 47 which passes through master manifold 88. Drive air distribution passage 47 and master manifold 88 is aligned and abutted to corresponding drive air distribution passages 47 in manifold 115 that abuts master manifold 88 as well as any other manifolds 115 which may subsequently be attached to respective manifolds 115 (FIGS. 3E and 10A). In this way, drive air is supplied to each of the manifolds 115.

Figure 7:
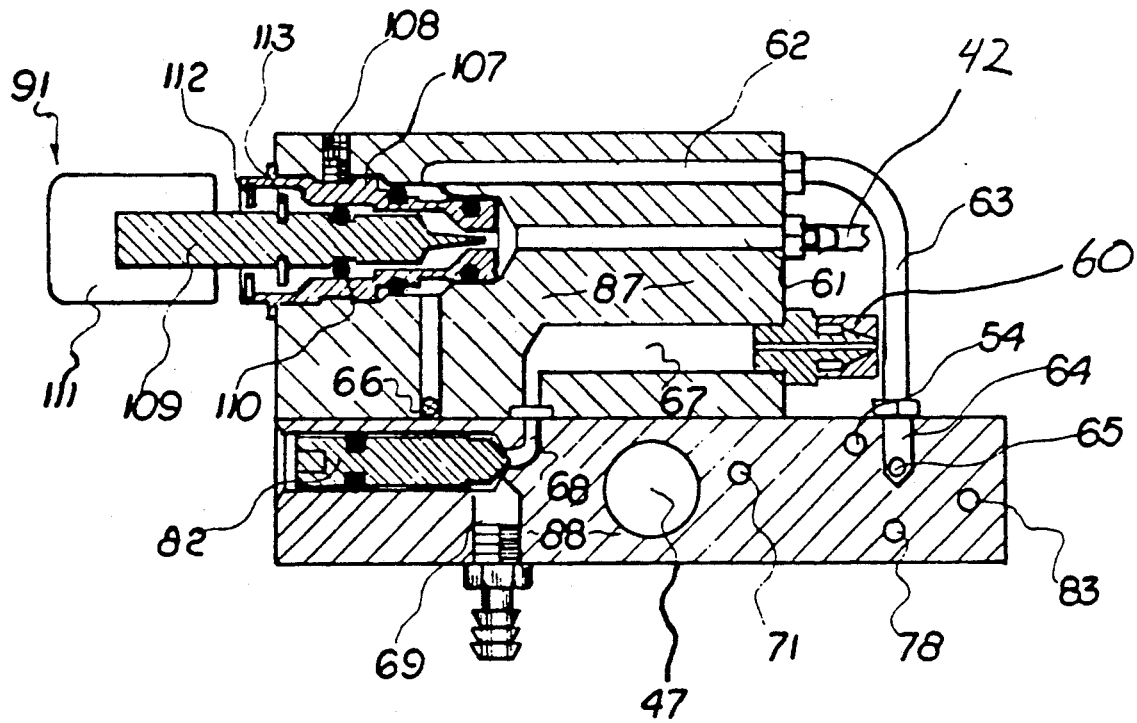
FIG. 7 is a cross-section taken along lines 7—7 in FIG. 3B showing a right side vertical cross-section view of chip air flow adjustment valve and its air passages, along with regulated air passages.
Figure 8:
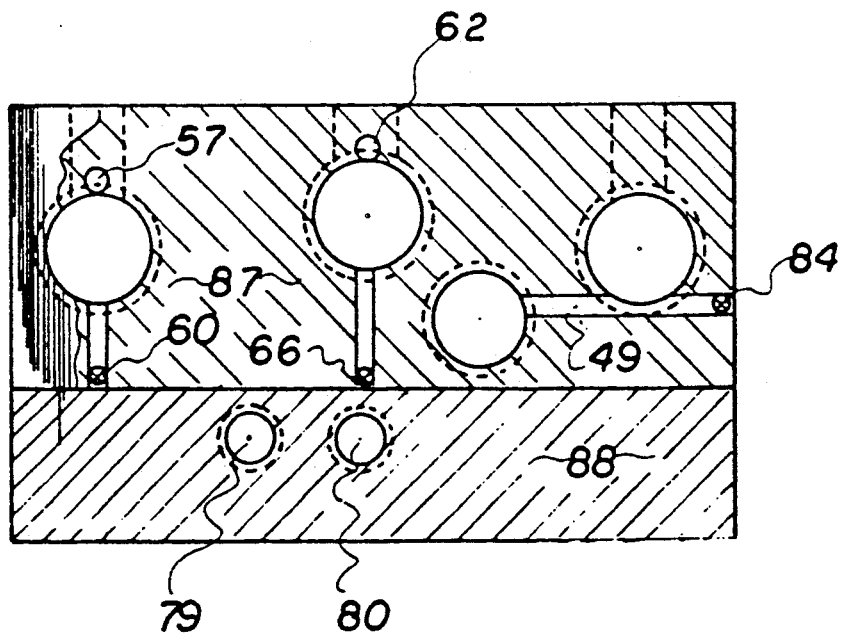
FIG. 8 is a cross-section taken along lines 8—8 in FIG. 3B showing a vertical cross-section view of valves and indicator housing, syringe flow adjustment screw housing and various air passages.
Figure 9:
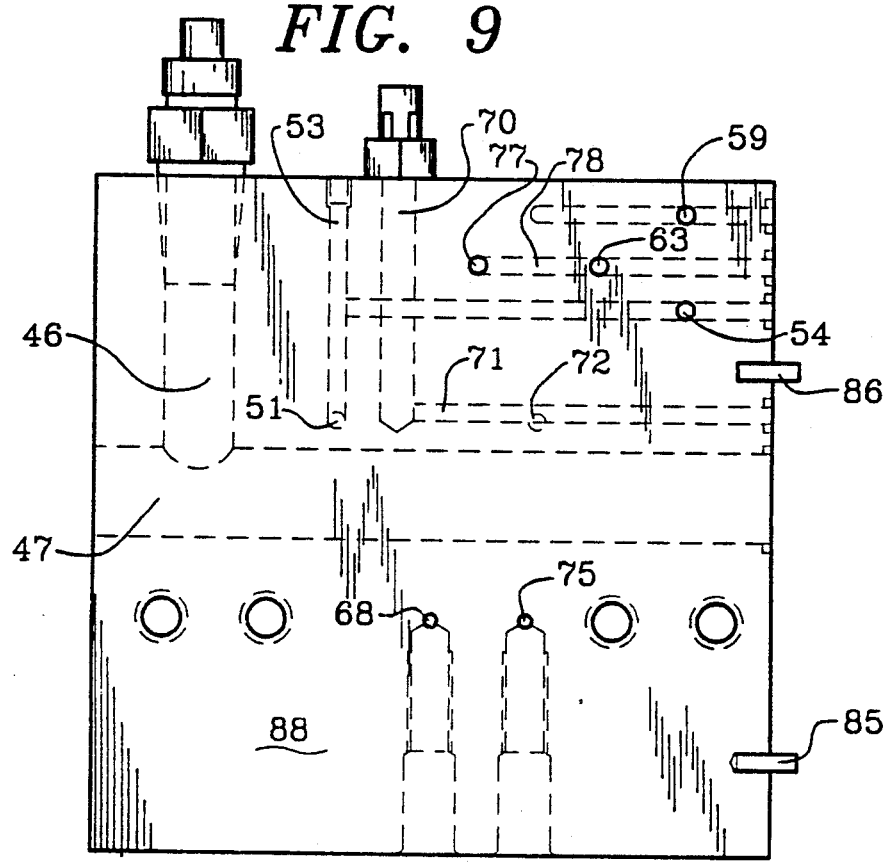
FIG. 9 is a cross-section taken along lines 9—9 in FIG. 3A is showing a top horizontal cross-section view of all air passages in master switch manifold.

Chip air is provided to the system through master module 87 and master manifold 88. Chip air from drive air foot control 43 passes through chip air line 42 (FIG. 1). When chip air button 44 is depressed, chip air travels through chip air line 42 to chip air inlet passage 61 in master module 87 (FIG. 7). Chip air inlet passage 61 is connected to chip air flow control valve 91 (FIGS. 3A and 7) which is a needle valve controlling the amount of air passing to passage 62 and subsequently out of master module 87 through chip air connecting tube 63. Chip air connecting tube 63 is connected to chip air distribution passage 65 within master manifold 88 (FIG. 7). Chip air distribution passage 65 extends through master manifold 88 into corresponding manifolds 115 so that chip air is provided throughout the system (FIG. 3E).

Figure 6:
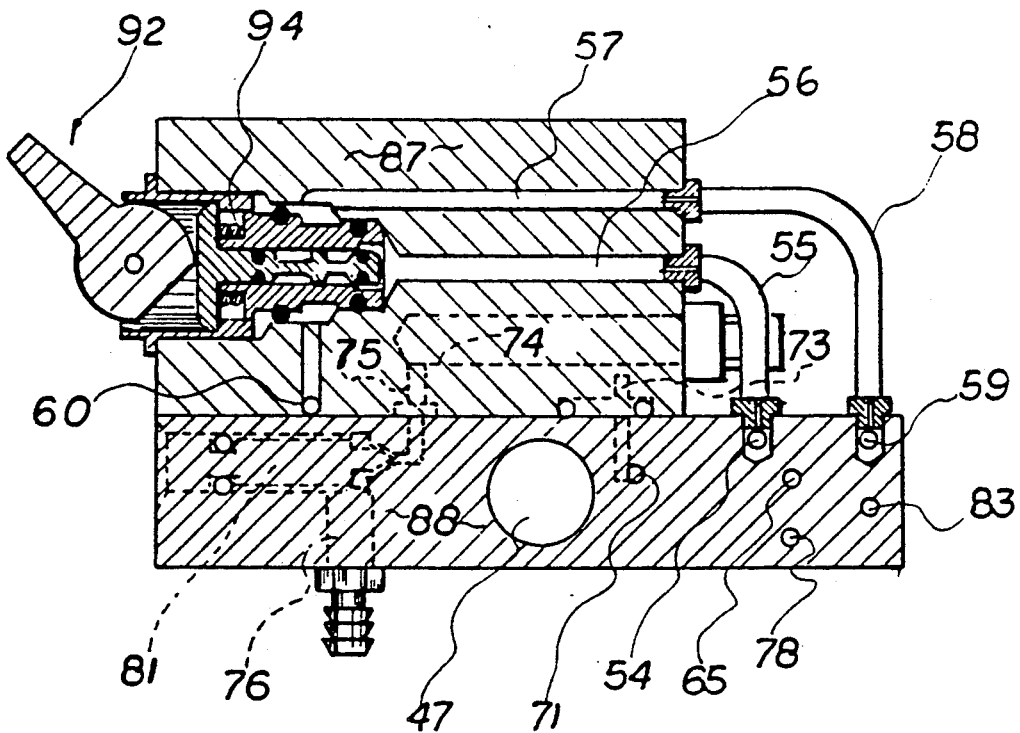
FIG. 6 is a cross-section taken along lines 6—6 in FIG. 3B showing a right side vertical cross-section view of wet/dry switch, wet/dry air, unregulated air and water passage.

Water enters master manifold 88 through water line 38 from supply box 12 (FIG. 3D). Water line 38 extends into master manifold 88 where contacts master manifold water passages 71 (FIG. 6) which extends out of master manifold 88 to connect with corresponding passages in the abutting control manifold 115. A passage 73 extends upward from water passage 71 to connecting passage 74 shown in FIG. 6. Connecting passage 74 connects passages 73 with passage 75 which then extends downward into master manifold 88 through syringe water metering screw 81 (FIGS. 3A and 6). Syringe water metering screw 81 controls the amount of water that passes to syringe water outlet 76 (FIGS. 3C and 6) which provides water to the syringe 221. In this way water is provided to the syringe through syringe water metering screw 81 and also to the handpieces 315 through passage 71 in the respective control modules 114 atop the control manifold 115 as will be explained hereafter.

Regulated air is provided to the syringe 221 through regulated air line 37 from supply box 12 (FIG. 1). This regulated air enters master module 87 through connector 60 as shown in FIGS. 3D and 7. This regulated air passes through passage 67, which is substantially horizontal, to downward directed passage 68 in master module 87 and master manifold 88 which in turn is connected to syringe air metering screw 82 (FIGS. 3A and 7). Syringe air metering screw 82 controls the amount of air available to syringe air outlet 69 as shown in FIGS. 3C and 7.

Figure 13:
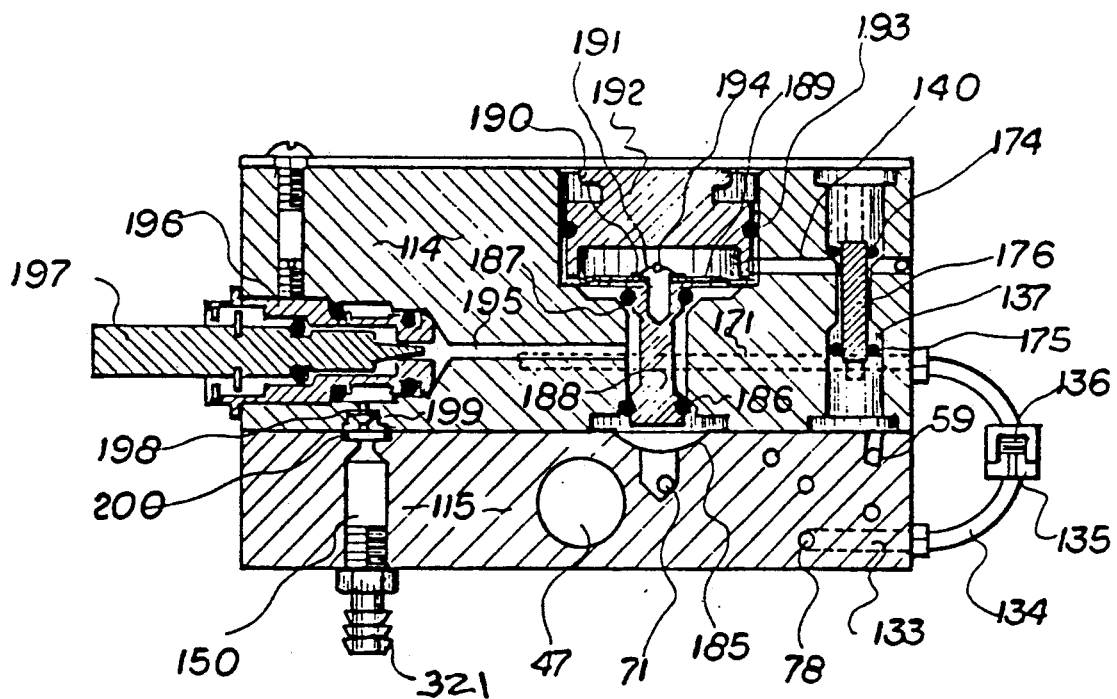
FIG. 13 is a cross-section taken along lines 13—13 in FIG. 11 showing a right side vertical cross-section view of water passages, AND-gate and piston valve, along with water coolant adjust valve and check valve. Also shown, pressure signal passages and check valve.

Air to power the water AND gate 137 passes through unregulated air line 54 in master manifold 88 as shown in FIGS. 5 and 6. A portion of this unregulated air leaves master manifold 88 through connecting tube 55 which connects master manifold 88 with passage 56 in master module 87. Passage 56 is connected to a water on/off switch 92 (FIGS. 3A and 6). Water on/off switch 92 is a pneumatic switch which controls the passage of air depending on the position of the toggle switch as is common in the art. Air from passage 56 is prevented from passing on/off switch 92 when it is in the closed position. However, when switch 92 is in its "on" position, air passes through switch 92 to passage 57 where it exists master module 87 through connecting tube 58 to enter master manifold 88. Air then proceeds through connecting passage 59 from master manifold 8 through corresponding connecting passage 59 in abutting control manifold 115. Passage 59 provides air pressure at the base of water AND gate 137 in control module 114 as shown in FIG. 13.

Figure 1C:
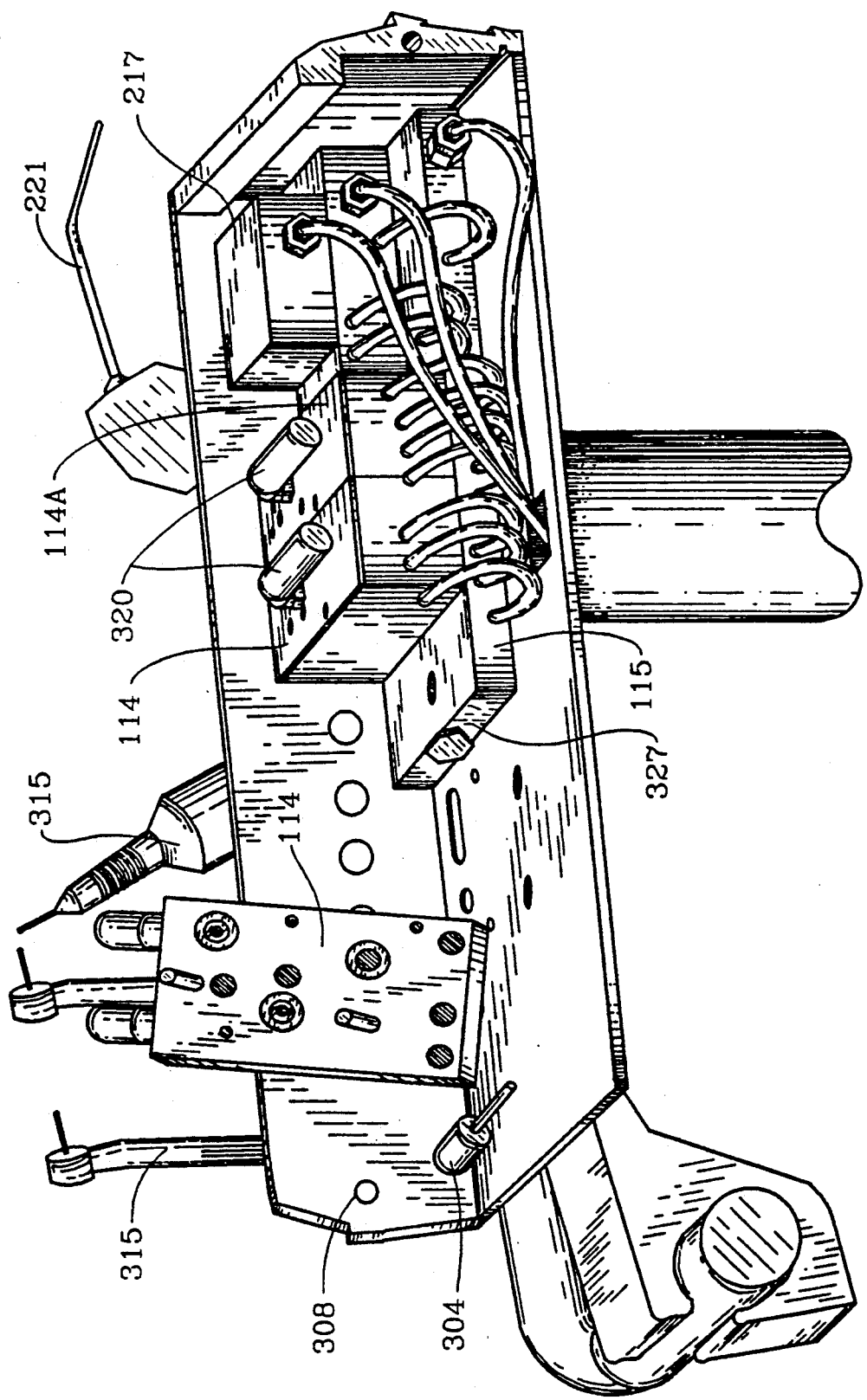
FIG. 1C is a rear view of the master switch module means and control module means with cover portions removed.

Each control module 114 corresponds to a handpiece 315 so that control of the functions of each handpiece 315 is controlled by a corresponding module 114. As shown in FIGS. 1E and 10A, each module 114 is attached to a corresponding manifold 115. In ordinary dental practice, each handpiece 315 has four lines attached to it: a drive air line, an exhaust air line, chip air/air coolant line; and a water line.

The drive air line supplies air to the turbine of the handpiece 315 to power the drill. The exhaust air line allows air which has passed through the turbine to exit the handpiece 315, to return to the control manifold 115, where it is passed through control module 114 ultimately to be vented to the atmosphere through a diffuser 320 (FIG. 1C).

The chip air/air coolant line provides a dual function. First, chip air may be provided to the handpiece tip by depressing chip air button 44 in order to provide a momentary "blast" of air through the end of the handpiece 315 to remove any debris which may have accumulated within the mouth of a patient. In addition, a constant supply of air coolant may be supplied through this line to be vented on the drill to cool it during the drilling operation. The amount of air coolant may be controlled as will be described hereafter.

Additionally, water is supplied to the handpiece 315 through the water tube to provide flushing and rinsing of the mouth cavity during dental operations.

The instant invention allows each module 114 to be activated by the removal of the handpiece 315 from the handpiece holder 208 (FIGS. 20–22) independently of whether any other handpieces 315 are within their respective holders 208 or not.

Exhaust air returning from the handpiece 315 through exhaust air tube enters the bottom of manifold 115 where it passes through manifold 115 into passage 173 (FIG. 10C) through module 114 (FIG. 10B) where it is vented through a diffuser 320 (FIG. 1C) into the atmosphere.

Figure 21:
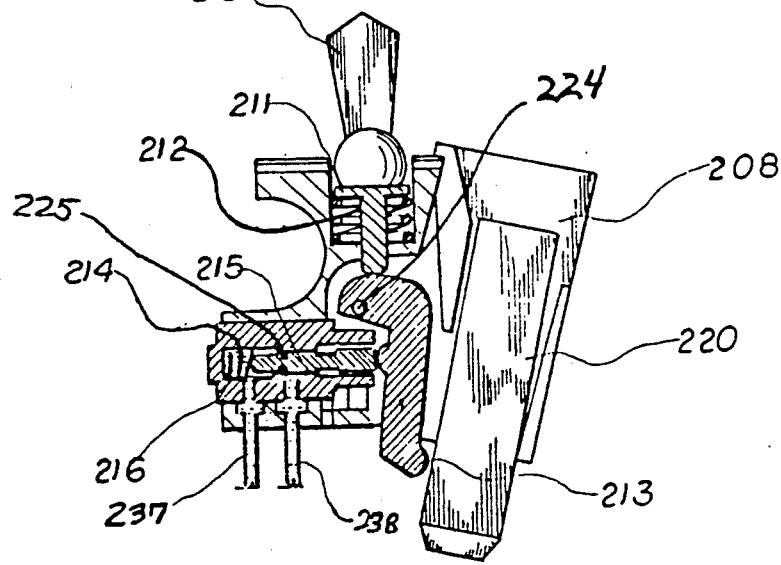
FIG. 21 is a cross-section taken along lines 21—21 in FIG. 20 showing a left side vertical cross-section view of handpiece holder switch assembly.
Figure 22:
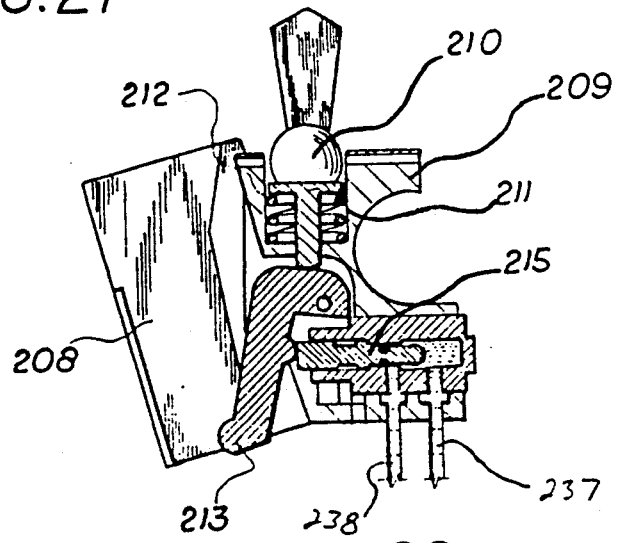
FIG. 22 is a cross-section taken along lines 22—22 in FIG. 20 showing a right side vertical cross-section view of handpiece holder switch assembly.
Figure 23:
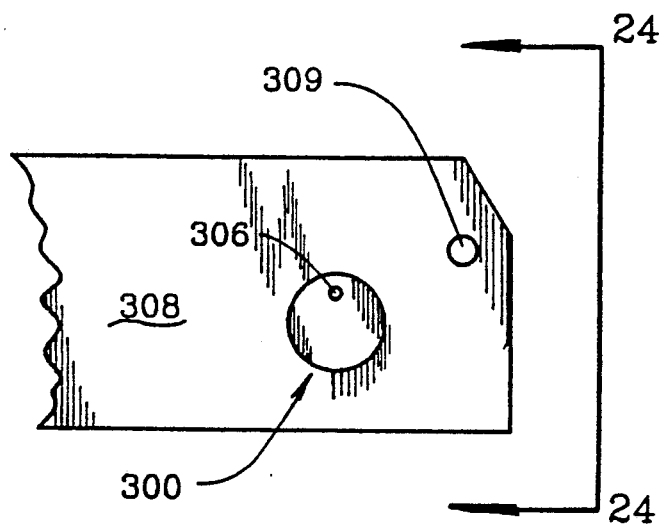
FIG. 23 illustrates a portion of the front panel that fits in front of the manifolds and blocks with control knob openings.
Figure 24:
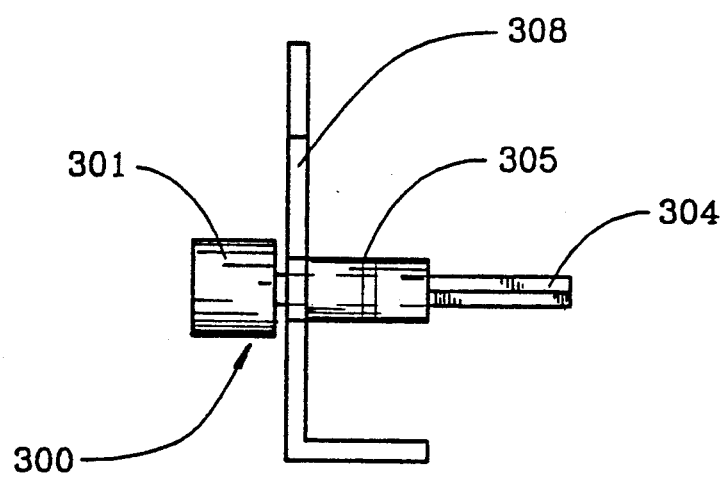
FIG. 24 is a side view taken along line 24—24 of FIG. 23 illustrating the mounting of the adjustment tool.
Figure 25:
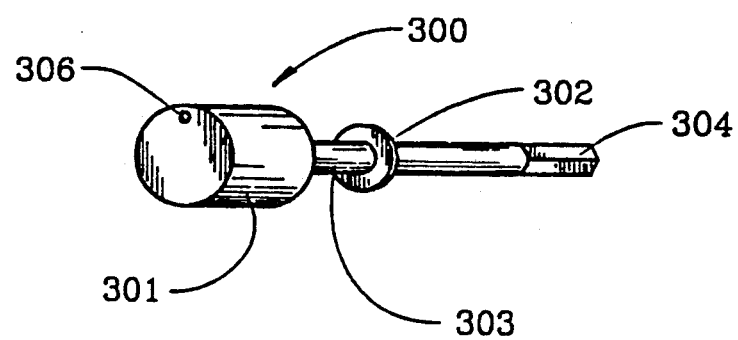
FIG. 25 is a perspective view of the adjustment tool.

Unregulated air passes through unregulated air distribution passage 54 in master manifold 88 to corresponding passages 54 in control manifolds 115. Thereafter, unregulated air leaves control manifold 115 through air outlet 117 (FIG. 10A) located on the bottom side of control manifold 115. Tubing connects air outlet 117 to air inlet 237 in handpiece holder switch 208 as indicated in FIGS. 21 and 22. In handpiece holder switch 208, a handpiece 315 may be secured within a tube shaped receptacle 220. Activator toggle 213 which pivots around a pivot point 224 is provided. Activator toggle 213 presses against spool valve 215 which extends into chamber 214. A spring 216 is provided within chamber 214 which pushes valve spool 215 against activator toggle 213 and biases activator toggle 213 away from chamber 214. Unregulated air from air outlet 117 enters chamber 214 through air inlet 237. Air within chamber 214 is prevented from moving down valve spool 215 by an O-ring seal 225 located along valve spool 215 which interacts with the walls of chamber 214 to provide an airtight seal.

When handpiece 315 is removed from receptacle 220 in handpiece holder switch 208, activator toggle 213 is moved outward by the biasing action of spring 216. As activator toggle 213 moves outward, valve spool 215 also moves outward moving O-rings 225 toward handpiece holder switch 208. As O-rings 225 move a sufficient distance past handpiece holder return signal outlet 238, air from unregulated air inlet 237 passes through chamber 214 into handpiece holder return signal outlet 238. Return signal outlet 238 is connected through tubing to return signal inlet 118 on control manifold 115 (FIG. 10A). In this way, the absence of a handpiece 315 within receptacle 220 is indicated by the presence of air pressure within return signal inlet 118 in manifold 115.

Figure 16:
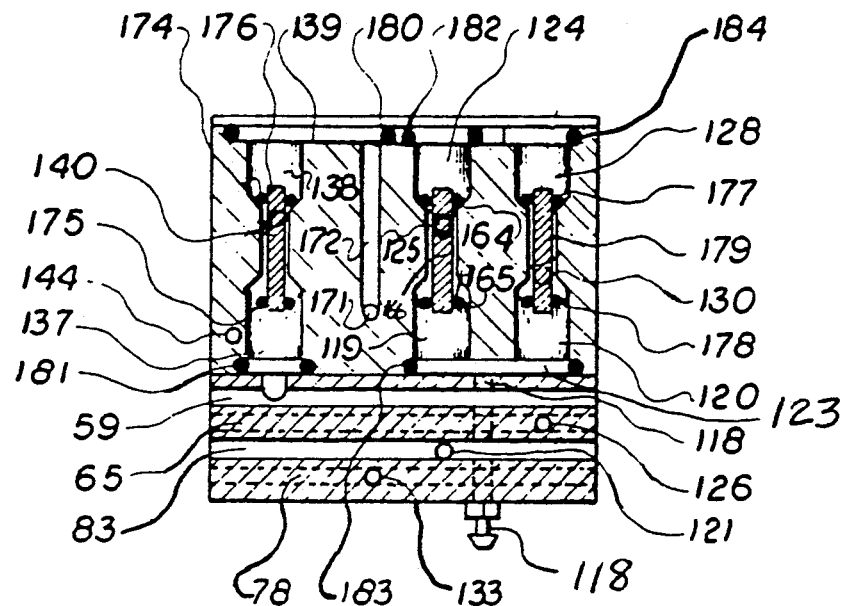
FIG. 16 is a cross-section taken along lines 16—16 in FIG. 11 showing a rear vertical cross-section view of all AND-gates in the closed position.

Handpiece holder return signal inlet 118 passes through manifold 115 and into control module 114 as shown in FIG. 16. Pressurized air from return signal inlet 118 enters chamber 123 which connects drive air AND gate chamber 119 and chip air AND gate chamber 120. Both AND gate chambers 119, 120 have a constricted middle section and an expanded upper section 124, 128, respectively. A cylindrical drive air piston 166 is located primarily within the constriction of drive air AND gate chamber 119. Drive air piston 166 has an upper O-ring 164 and a lower O-ring 165 at its opposite ends a small distance outside of constricted drive air AND gate chamber 119. Upper and lower O-rings 164, 165 are located along drive air piston 166 a sufficient distance so that if one set of O-rings is in contact with the constricted portion of drive AND gate chamber 119, and the other O-ring will be away from the constriction thereby allowing air to pass around the O-ring not in contact and enter the constricted portion of drive air AND gate chamber 119.

Likewise, in chip air AND gate chamber 120, a cylindrical chip air piston 179 is provided primarily in the constricted portion of chip air AND gate chamber 120. Chip air piston 179 has an upper O-ring 177 and a lower O-ring 178. O-rings 177, 178 are located along chip air piston 179 outside of the constriction of chip air AND gate chamber 120 so that when one set of O-rings 177, 178 is in contact with the constricted portion of chip air AND gate chamber 120, the other set of O-rings is away from the constricted portion thereby allowing air to pass around the O-ring not in contact with the constriction and enter the constricted portion of chip air AND gate chamber 120.

Figure 12:
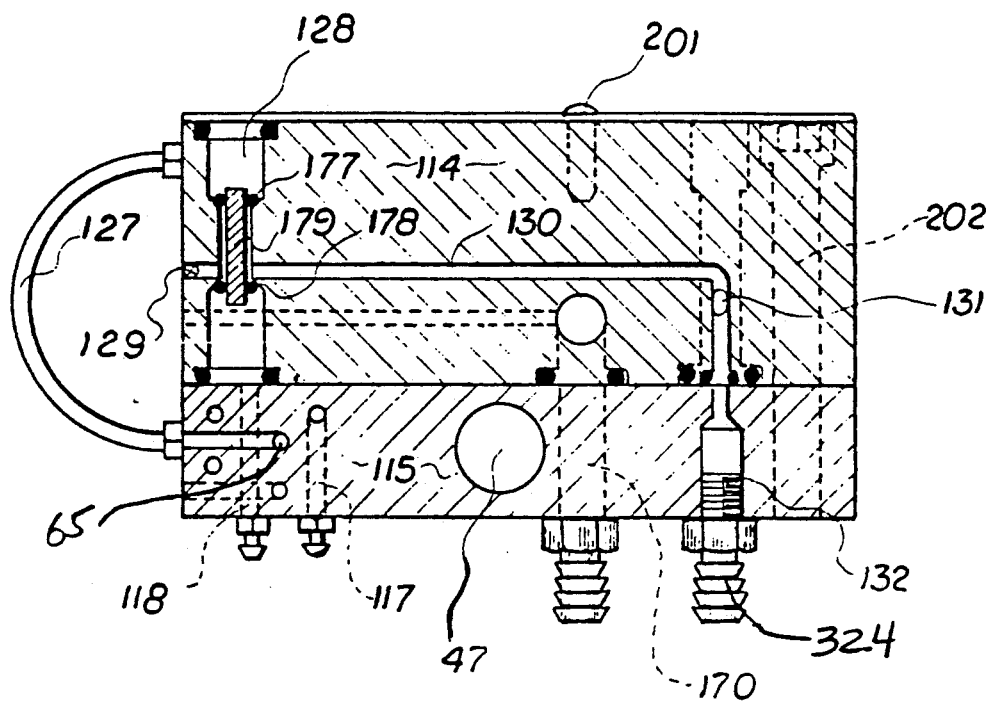
FIG. 12 is a cross-section taken along lines 12—12 in FIG. 11 showing a left side vertical cross-section view of chip air AND-gate and passages. Also shown are drive air, unregulated air, pressure signal air, air coolant and handpiece hanger return signal passages.
Figure 17:
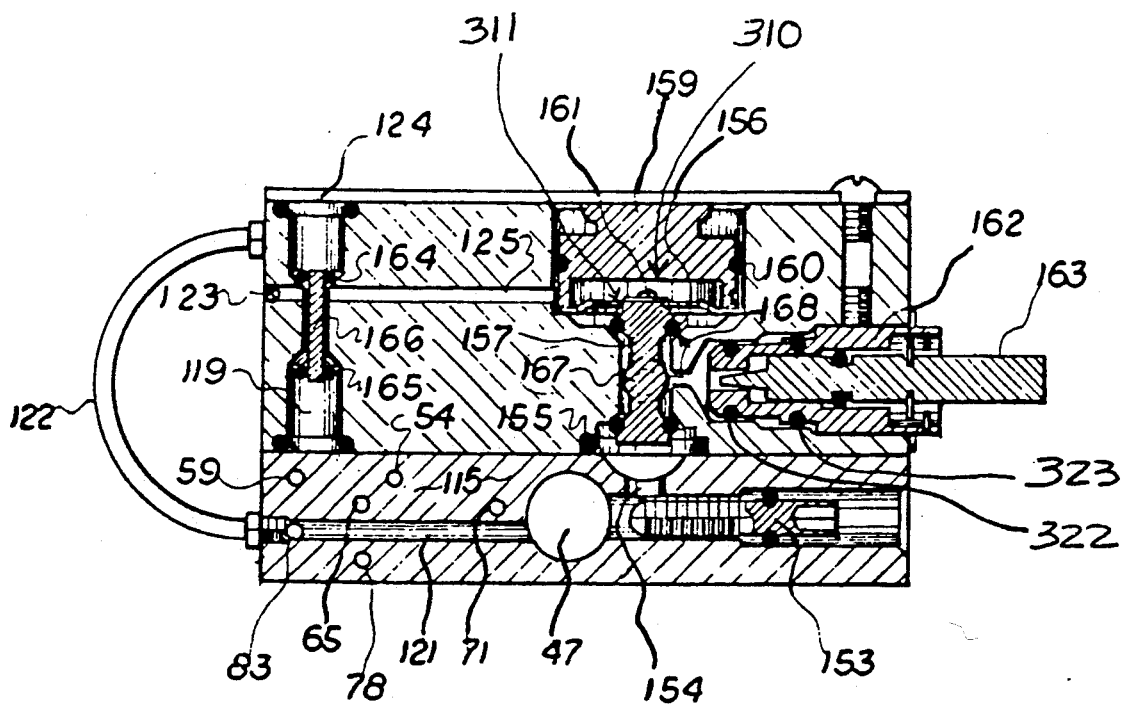
FIG. 17 is a cross-section taken along lines 17—17 in FIG. 11 showing a left side vertical cross-section view of drive air passages, AND-gate flow adjustment screw and piston valve showing it in the closed position. Also shown, is the air coolant valve and passages.

Expanded upper section 124 is connected to drive air distribution passage 47 in manifold 115 through tube 122 (FIGS. 10A and 17) and passage 121 also located in manifold 115 (FIG. 17). Expanded upper section 128 is connected to chip air distribution passage 65 in manifold 115 through tube 127 (FIGS. 10A and 12).

When air pressure is present within chamber 123 from return signal inlet 118, drive air piston 166 and chip air piston 179 are pushed upward by the unregulated air pressure so that lower O-rings 165 and 178 are seated against the constriction of respective drive air AND gate chamber 119 and chip air AND gate chamber 120.

Because the air within chamber 123 comes from unregulated air line 39, this air is at the maximum pressure provided by compressor 25. By contrast, both drive air and chip air, which are supplied to expanded upper sections 124 and 128, have passed through regulator 35 which reduces the air pressure to a pressure lower than the unregulated air pressure. As a result, although pressurized air may be present on both sides of pistons 166, 179 respectively, the higher pressure of the unregulated air will be present at the bottom of pistons 166, 179. This unregulated air will push pistons 166, 179 upward to seat O-rings 165, 178 respectively against the constricted portions of AND gates 119, 120 respectively.

When pistons 166, 179 move upward air under pressure within the top chambers 124, 128 of drive air AND gate chamber 119 and chip air AND gate chamber 120, respectively, which is regulated air, moves past upper O-rings 164, 177 into the constricted portion of respective AND gate chambers 119, 120.

As seen in FIG. 17, a passage 125 extends from the constricted portion of drive air AND gate chamber 119 into plunger chamber 159 which has an expanded upper portion and a constricted lower portion. A plunger 310 is located within plunger chamber 159. Plunger 310 has a diaphram 311, located within the upper portion of plunger chamber 159 and a drive air piston 157 which is located primarily within the lower portion of plunger chamber 159. Surrounding drive air piston 157 at its upper end is upper O-ring 168. Surrounding drive air piston 157 at its lower end is lower O-ring 155. The lower portion of plunger chamber 159 is connected to drive air distribution passage 47 through passage 154 (FIG. 17).

When unregulated air is not present in chamber 123, drive air enters the lower portion of plunger chamber 159 where it pushes against the bottom of drive air piston 157. Because drive air is also presented to expanded upper section 124, which pushes piston 166 downward seating upper O-rings 164 against the constricted portion of chamber 119, no corresponding pressure is presented to the upper portion of plunger chamber 159 through passage 125.

As stated, air present within drive air distribution passage 47 in control manifold 115 moves through passage 121 in manifold 115 to tube 122 which connects drive air to the top of drive air AND gate chamber 124. As pistons 166, 179 are pushed upward by air in chambers 119, 120 from handpiece holder switch 208, this drive air then moves downward past upper O-rings 164 which have been moved upward through the movement of piston 166 and into passage 125. Thereafter, the drive air enters the upper portion of plunger chamber 159 where it depresses diaphragm 311 pushing driver piston 157 downward into the lower portion of plunger chamber 159. Upper O-ring 168 forms an airtight seat with the lower portion of plunger chamber 159 when plunger 310 is pushed downward by air pressure chamber 159. The depression of plunger 310 pushes lower O-ring below the lower portion of plunger chamber 159.

Figure 15:
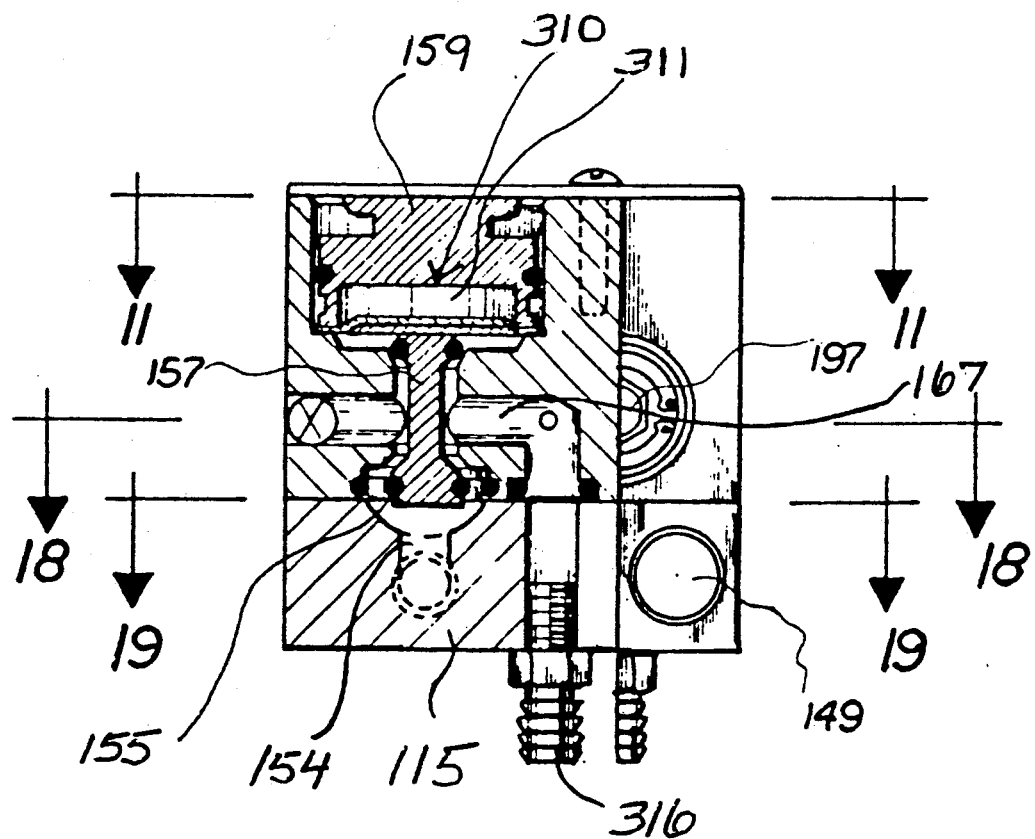
FIG. 15 is a cross-section taken along lines 15—15 in FIG. 11 showing a front vertical cross-section view of drive air piston valve in the open position and passages.

The lower portion of plunger chamber 159 is connected to drive air distribution passage 47 through passage 154 as shown in FIGS. 15 and 17. The amount of air that may pass through passage 154 into the lower portion of plunger chamber 159 is controlled by flow pressure adjustment screw 153. When plunger 310 is not depressed by the presence of air pressure within the upper portion of plunger chamber 159, air pressure from drive air distribution passage 47 pushes plunger 310 upward so that lower O-ring 155 comes into contact with the lower portion of plunger chamber 159 in an airtight seal. When plunger 310 is depressed due to air pressure in the upper portion of plunger chamber 159, air from drive air distribution passage 47 moves upward through passage 154 past lower O-rings 155 into horizontal passage 167 as shown in FIG. 15. Thereafter, passage 167 makes a ninety degree turn downward through manifold 115 to an external connection 316 which allows a tube from the handpiece 315 to be attached so that drive air is presented to the handpiece 315.

Because plunger 310 has a diaphram 311 at its top (FIG. 17), the presence of pressurized air within plunger chamber 159 causes greater force on plunger 310 by pressing on diaphram 311 than the force applied to the bottom of plunger 310 by drive air from passage 153. This force difference causes plunger 310 to move downward whenever pressurized air is present in plunger chamber 159.

Figure 18:
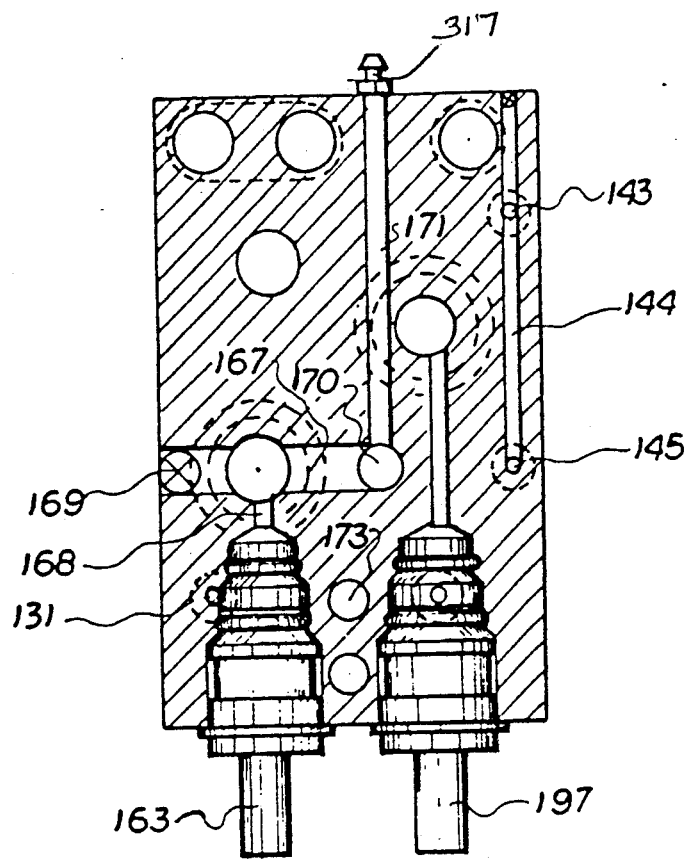
FIG. 18 is a cross-section taken along lines 18—18 in FIG. 15 showing a top horizontal cross-section view of control module air and water coolant flow control valves.
Figure 19:
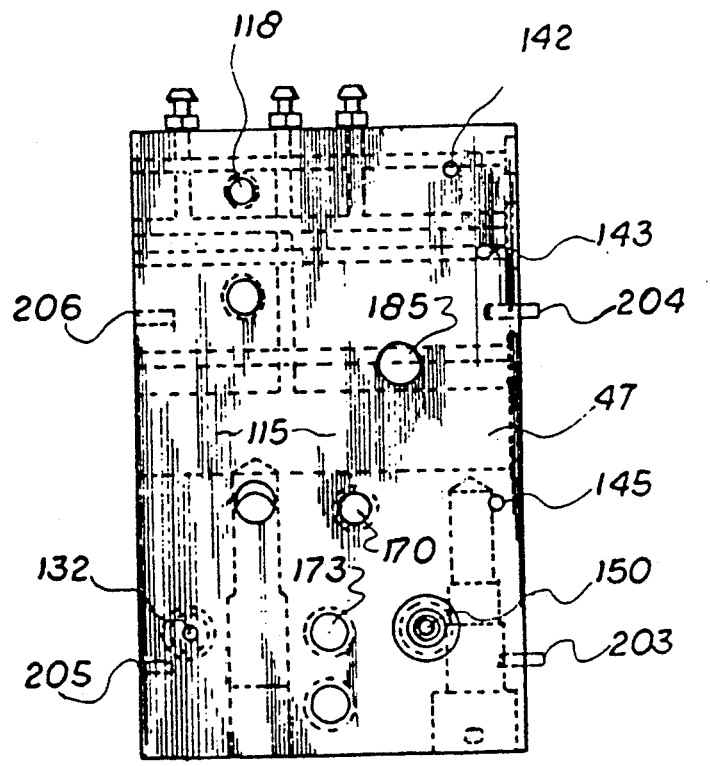
FIG. 19 is a cross-section taken along lines 19—19 in FIG. 15 showing a top view of control manifold and all of its passages.
Figure 20:
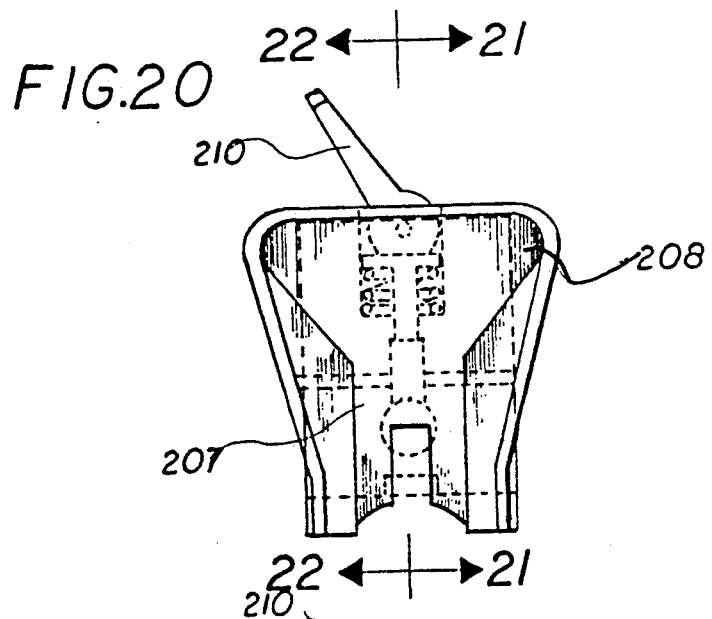
FIG. 20 is a front view of handpiece holder switch.

Connected to passage 167 is a narrow horizontal passage 171 (FIG. 18) which extends toward the rear of the control module 114, and exits module 114 through connector 317. Attached to passage 171 at connector 317 is tube 134 (FIGS. 10D and 13) which connects passage 171 to passage 133 in manifold 115. Passage 133, in turn, is connected to passage 78 which passes through manifolds 115 into master manifold 88. There, passage 78 is connected to a pressure gauge 217 on master module 87 which indicates the drive pressure applied to the turbine powered drill in the handpiece 315. A check valve 135 is provided intermediate tube 134 to allow air from passage 171 to pass in only one direction into passage 78. This check valve 135 prevents air under pressure in passage 78 from passing back through tubes 134 into additional modules 114 which may not be activated by the removal of their respective handpieces 315 as described above. Air passing from tubes 134 into modules 114 which have not been activated by the removal of their respective handpieces 315 would cause plunger 193 in the non-enabled module 114 to be depressed thereby activating water to the non-enabled handpiece 315. Further, air would pass through air coolant flow control valve 163 in the non activated module 114 out to the non-enabled handpiece 315 thereby leaking air through this non-enabled handpiece 315. Therefore, it is beneficial to prevent air from leaving passage 78 and entering a non-enabled module 114.

Extending upward from passage 171 is passage 172 (FIG. 16) which connects passage 171 to a chamber 139 which leads to the upper portion 138 of water AND gate chamber 137. Water AND gate chamber has a centrally located constricted portion containing a piston 140 having upper and lower O-rings 174, 175, respectively, located along piston 140 outside the constricted portion of water AND gate chamber 137. The lower end of water AND gate chamber 137 is connected to manifold 115 which connects water AND gate chamber 137 to passage 59 (FIGS. 13 and 16).

Passage 59 is connected to the bottom of water AND gate chamber 137 (FIGS. 13 and 16). Unregulated air in passage 59 is present whenever water on/off switch 92 is in the "on" position as described above. When there is air pressure present in the lower portion of water AND gate chamber 137 from passage 59, piston 176 is biased upward by pressure from passage 59 so that lower O-rings 175 are seated against the constricted part of water AND gate 137. When the drive air AND gate is activated as described above, air pressure is present in the upper chamber 138 through passages 172, 171 and 167 from the drive air distribution passage 47. Then, drive air from passages 172, 171 and 167 passes over lower O-ring 175 through the constricted part of water AND gate chamber 137 to exit through passage 140 into water chamber 192. Water chamber 192 has an enlarged upper portion and a constricted lower portion. Located within water chamber 192 is a plunger 193 comprising a diaphragm 194 and a piston 188. Piston 188 is located within the constricted lower portion of water chamber 192 and has an upper and lower set of O-rings 186, 187 along its length outside of the constricted portion of water chamber 192.

Connected to the bottom of water chamber 192 is water connecting passage 71 located in manifold 115. When control module 114 is placed on manifold 115, water may flow through water connecting passage 71 into the lower portion of water chamber 192. If there is no air pressure acting on diaphragm 194, the pressure of the water from water passage 71 pushes piston 188 upwards so that lower O-rings 186 come into sealing contact with the narrow lower portion of water chamber 192. However, when air is present in water chamber 192 through passage 140, thereby depressing the plunger 193, upper O-rings 187 are brought into contact with the constricted narrow portion 192 and lower O-rings 186 are depressed a sufficient distance to allow water from a water passage 71 to flow around lower O-rings 186 and into the narrow constricted part of water chamber 192. Thereafter, water may exit the lower portion of water chamber 192 through passage 195, through water flow control valve 196 and out of passage 198 to a check valve 199 located on the bottom of module 114. Water flow control valve 196 is a needle valve such as is common in the art which allows the amount of water flowing through it to be regulated. Check valve 199 allows water to flow only out of module 114.

Abutted to check valve 199 at the base of module 114 is water passage 150 in manifold 115. Water passage 150 extends entirely through manifold 115 to an external connection 321 which allows tubing to connect connection 321 to the handpiece 315 thereby presenting water to handpiece 315.

Figure 14:
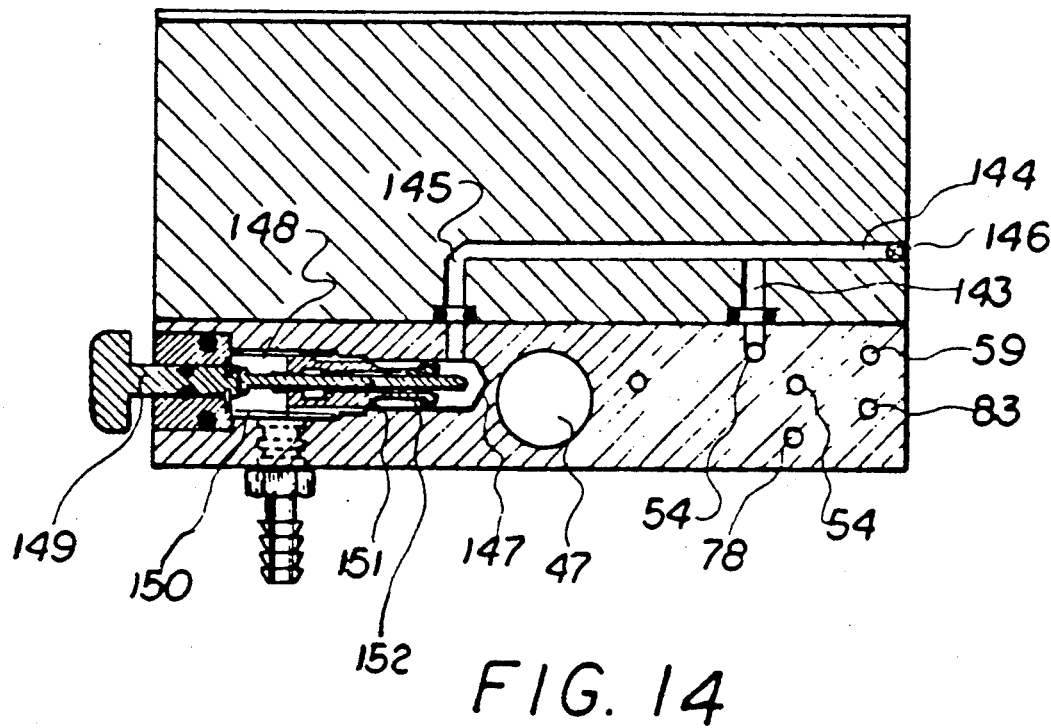
FIG. 14 is a cross-section taken along lines 14—14 in FIG. 11 showing a right side cross-section view of unregulated air passage, also the purge button and component.

Also connected to water passage 150 in manifold 115 is Schrader valve 151 (FIG. 14) which has an actuator button 149 attached. Schrader valve 151 is connected to passage 145 located in module 114. Passage 145 is connected to unregulated air line 54 in manifold 115 so that a constant source of pressurized air is supplied through passage 145 to Schrader valve 151. Depressing button 149 on Schrader valve 151 permits air under pressure to pass through Schrader valve 151 into water passage 150 thereby dispelling water out of water passage 150 through connection 321 through the tubing to the handpiece 315. It is to be noted in this context, that check valve 199 prevents water under pressure from the air passing through Schrader valve 151 from passing back into module 114. It is also to be noted that because of the constant source of air pressure present at Schrader valve 151 from unregulated air line 54, depressing button 149 will always send air into connection 321 through water passage 150 whether or not handpiece 315 is in its place within receptacle 220 or not.

Returning to the chip air control, unless handpiece holder switch 208 has a handpiece 315 removed from receptacle 220, module 114 is inactivated as explained above because no air signal in the form of pressurized air is present at return signal inlet 118. The pressure within the upper chamber 128 of chip AND gate 120 from chip air distribution passage 65 via chip air connecting tube 127 (FIG. 12) pushes piston 179 downward so that upper O-rings 177 are in airtight contact with the constriction of chip AND gate chamber 120. However, when the handpiece 315 is removed from receptacle 220 in handpiece holder switch 208, air from return signal inlet 118 enters the lower chamber of chip AND gate 120 and pushes piston 179 upward. As piston 179 is pushed upward, lower O-rings 178 are brought into contact with the constricted portion of chip AND gate 120. This allows chip air from chip air connection tube 127 to move downward in the upper portion of chip AND gate 120 past upper O-rings 170 and into the constricted portion of chip AND gate 120.

Connected to the constricted portion of chip AND gate 120 is passage 130 (FIG. 12) which extends forward of the constricted portion of chip AND gate 120 at a position in module 114 even with air coolant flow control valve 163 (FIG. 17). Thereafter, passage 130 makes a ninety degree downward turn as shown in FIG. 12. Passage 131 connects passage 130 in the downward directed part of passage 130 with the chamber containing air coolant flow control valve 163. Air coolant flow control valve 163 opens to passage 167, which may pass drive air as explained above, through passage 168. An O-ring 322 provides an airtight seal with the end of air coolant flow control valve 163 closest to passage 167 and passage 168. When air coolant flow control valve 163 is opened, air may enter it from passage 168 and exit along the side of air coolant flow control valve 163 into opening 131. A second O-ring 323 is provided along air coolant flow control valve 163 to seal the air leaving air coolant flow control valve 163 into opening 131. These O-rings ensure that all the air leaving air coolant flow control valve 163 will exit through through opening 131 into passage 130. In this way, air from the drive air passage 167 may be directed into passage 130 downward to manifold 115 and out through external connection 324 (FIG. 12). Tubing may be attached to connection 324 and to handpiece 315 to provide air coolant to handpiece 315 to cool the drill when the drill is operating due to drive air (from passage 167) powering the turbine drill. In this way air coolant is provided to the drill in handpiece 315 whenever the drive air is activated, as described above, and the air coolant flow control valve 163 is opened to allow air coolant into passage 130.

Figure 1D:
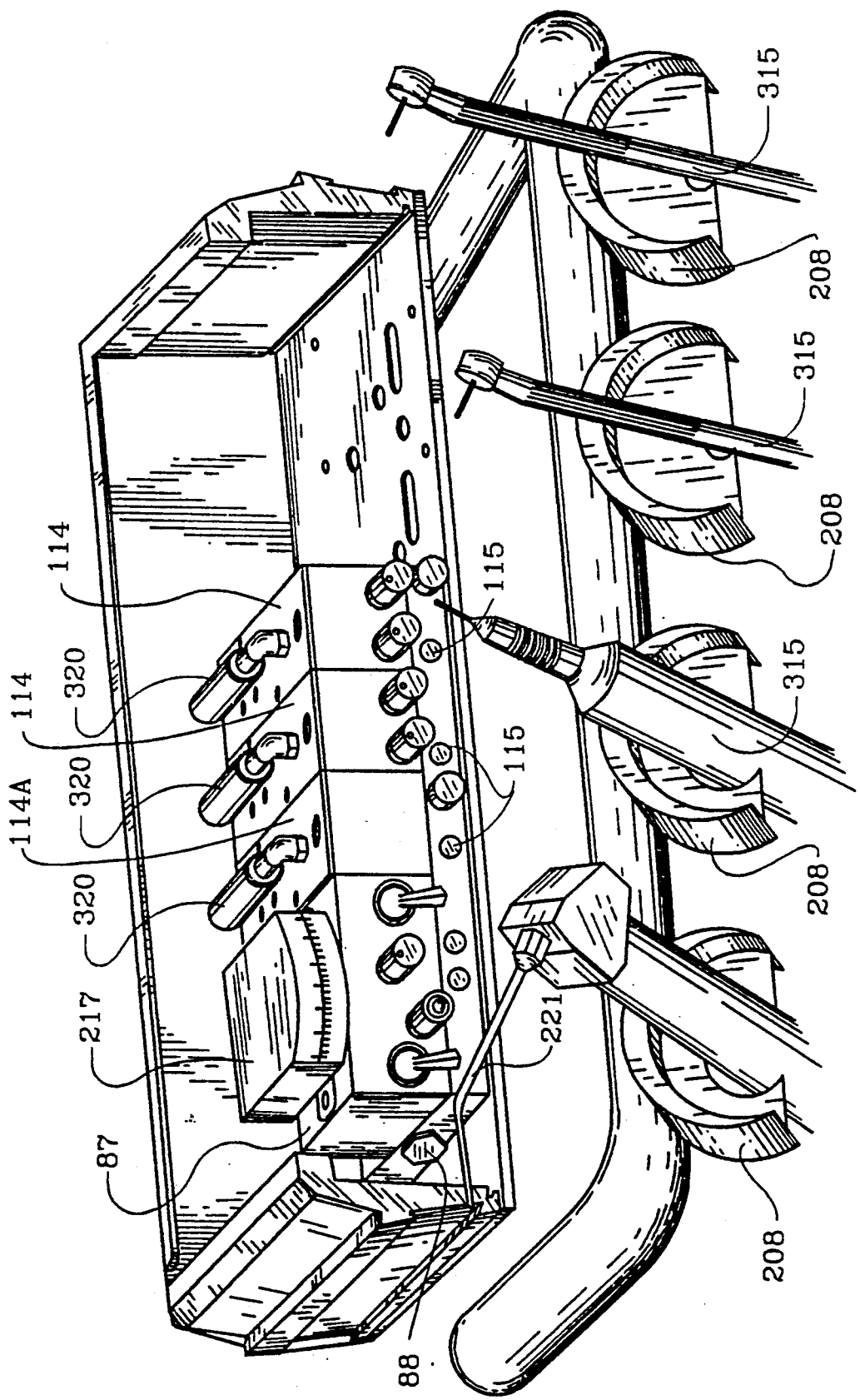
FIG. 1D is a front view of FIG. 1C with the front and top cover portions removed.
Figure 1E:
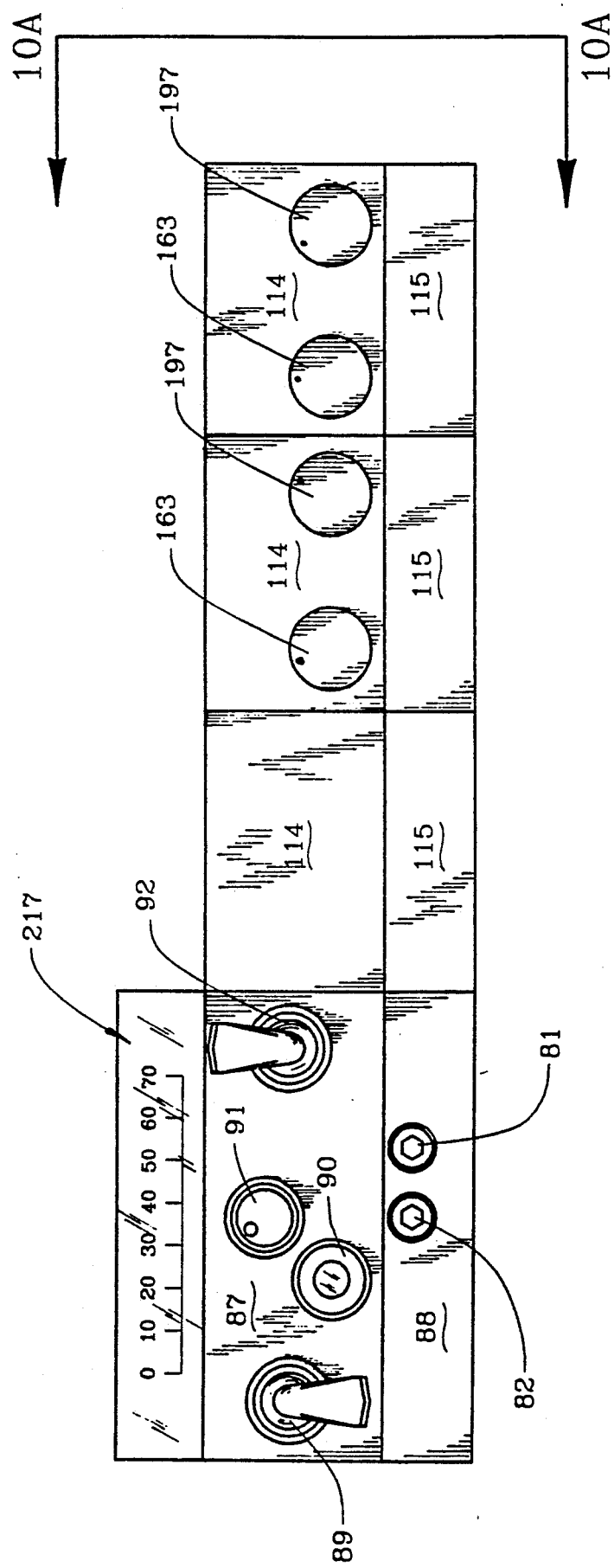
FIG. 1E is a front view of the working components illustrated in FIG. 1B removed from the housing to provide an illustration of the various modules and their respective manifolds.

The control functions described above in connection with a specific control module 114 attached atop a corresponding control manifold 115, which together cooperate to control the functions of a corresponding handpiece 315 may be duplicated by additional control modules 114 and control manifolds 115 which will control their respective corresponding handpieces 315 (FIGS. 1D and 1E). The respective additional control manifolds 115 are abutted to the currently used control manifolds 115 so that the respective passages in the control manifold 115 described above and shown in FIG. 10A are aligned and placed in sealing contact with the corresponding passages in the added control manifold 115 so that the passages may continuously pass water or air from one control manifold 115 to the other.

At the edge of the control manifold 115 furthest from the master manifold 88, whether there is one or many manifolds 115 in use, an end plate 327 (FIG. 1C) must be attached to the last manifold 115 to seal the passages. The end plate 327 is preferably a plate attached to the furthest edge of the manifold 115 furthest from master manifold 88.

The foregoing has been a description of the preferred embodiment of the invention. The description has been given by means of example and not for limitation. It is clear that changes and modifications may be made to the described invention and still be within the scope of the attached claims. Further, obvious changes and modifications will occur to those skilled in the art.

What is claimed is:

1. A pneumatic dental hand piece function control system attached to a source of pressurized air and water, comprising:
    a master control module comprising integral fluid conveyance means disposed therein for fluidly communicating with a supply of unregulated air, chip air, and regulated air, and for transporting said supply of unregulated air, chip air, and regulated air therethrough, said master control module further comprising therein, first valve means connected to said fluid conveyance means for interrupting said unregulated air supply and for enabling a signal air return for initiating a supply of water and said regulated air, second valve means connected to said fluid conveyance means for modulating said chip air supply, and third valve means connected to said fluid conveyance means for enabling a water initiating air signal;
    a master manifold disposed adjacent said master switch module, said master manifold comprising integral fluid conveyance means disposed therein for fluidly communicating with said supply of unregulated air, chip air, and water initiating air signal from said master control module, a supply of dry air, water, and a return air pressure signal, and for transporting said unregulated air, chip air, water initiating air signal, drive air, water, and return air pressure signal therethrough;
    at least one secondary manifold comprising integral fluid conveyance means disposed therein for fluidly communicating with said master manifold, and for transporting said unregulated air, chip air, water initiating air signal, drive air, water, and return air pressure signal therethrough;
    at least one air control module releasably attached to said secondary manifold comprising integral fluid conveyance means for fluidly communicating with said secondary manifold, and for transporting said unregulated air, drive air, and return air pressure signal therethrough, said secondary control module further comprising first air valve means for enabling the flow of said drive air to said hand piece;
    at least one air and water control module releasably attached to said secondary manifold comprising integral fluid conveyance means for fluidly communicating with said secondary manifold, and for transporting said unregulated air, drive air, return air pressure signal, water, and water initiating air signal therethrough, said air and water control module having first air valve means for enabling the flow of said drive air to said hand piece, second air valve means for enabling the flow of said chip air to said hand piece, and water valve means for enabling the flow of said water to said hand piece; and
    at least one holding means for releasably securing said respective dental hand piece, said holding means further including integral pneumatic switching means attached to said first and second air valve means and water valve means for detecting the absence of said hand piece from said holder, whereby said first and second air valve means, and said water valve means disable the flow of said drive air, chip air, and water to said hand piece.

2. The pneumatic control system recited in claim 1, further comprising foot switch means for enabling the flow of drive air and chip air to said master manifold and master control module respectively.

3. The pneumatic control system recited in claim 1, wherein said first air valve means comprise:
    an air AND gate having inputs fluidly connectible to said unregulated air and said drive air from said air control module fluid conveyance means, and an output of said drive air; and
    an air plunger valve having an actuator input of said drive air from said AND gate and an input and output of said drive air from said air control module fluid conveyance means, whereby activating said pneumatic switching means causes the introduction of unregulated air into said AND gate which in turn enables drive air to flow into said plunger valve thereby allowing the flow of drive air to said hand piece through said plunger valve output and said air control module fluid conveyance means.

4. The pneumatic control system recited in claim 1, wherein said second air valve means comprise:
    an air AND gate having inputs fluidly connectible to said unregulated air and said chirp air from said air and water control module fluid conveyance means, and an output of said chirp air thereby allowing the flow of chirp air to said hand piece through said AND gate output and said air and water control module fluid conveyance means.

5. The pneumatic control system recited in claim 1, wherein said water valve means comprise:
   an air AND gate having inputs fluidly connectible to said unregulated air and said water initiating air signal from said air and water control module fluid conveyance means, and output of said water initiating air signal; and
   a water plunger valve having an actuator input of said water initiating air signal from said AND gate and an input and output of said water from said air and water control module fluid conveyance means, whereby activating said pneumatic switching means causes the introduction of drive air into said AND gate which in turn enables drive air to flow into said plunger valve thereby allowing the flow of water to said hand piece through said water valve output and said air and water control module fluid conveyance means.

6. The pneumatic control system recited in claim 1, wherein said master control module first and second valve means are a pneumatic toggle switch.

7. The pneumatic control system recited in claim 1, wherein said master control module, master manifold, secondary manifold, air control module, and air and water control module fluid conveyance means are integrally molded passageways within said respective manifolds and modules.

8. The pneumatic control system recited in claim 1, further comprising an air pressure gauge fluidly connected to said air pressure signal and said master manifold fluid conveyance means for displaying the drive air pressure introduced to a turbine disposed within said hand piece.

9. The pneumatic control system recited in claim 1, further comprising exhaust means attached to said hand piece for venting said hand piece drive air.

10. The pneumatic control system recited in claim 9, wherein said exhaust means comprise:
    an exhaust conveyance line fluidly connected to said hand piece and in fluidic communication with said secondary manifold; and
    a diffuser fluidly connected to said secondary control module whereby said exhaust may flow from said hand piece through said secondary manifolds and attached respective control modules and out to the ambient air through said diffuser.

11. The pneumatic control system recited in claim 1, wherein said secondary air and water control module further comprises a Schraeder valve fluidly connected to said air and water control module fluid conveyance means for purging accumulated water within said hand piece.

12. The pneumatic control system recited in claim 1, wherein said master manifold further comprises flow adjustment means fluidly connected to said master manifold fluid conveyance means for modulating the flow of said water and regulated air to the ambient.

13. The pneumatic control system recited in claim 1, wherein said air control module further comprises flow adjustment means fluidly connected to said air control module fluid conveyance means, for modulating the flow of said drive air to said respective hand piece.

14. The pneumatic control system recited in claim 1, wherein said air and water control module further comprises flow adjustment means fluidly connected to said air and water control module fluid conveyance means, for modulating the flow of said drive air, chip air, and water to said respective hand piece.

15. The pneumatic control system recited in claim 11, wherein said air and water control module further comprises check valve means fluidly associated with said air and water control module fluid conveyance means between said water flow adjustment means and said hand piece for preventing the reverse flow of water upon actuation of said Schraeder valve.

16. The pneumatic control system recited in claim 7, wherein said pneumatic control system further comprises check valve means fluidly connected between said air and water control module fluid conveyance means return air pressure signal and said secondary manifold fluid conveyance means return air pressure signal for preventing the reverse flow of said pressure signal air.

* * * * *